US008829455B2

(12) United States Patent
Nakatsugawa et al.

(10) Patent No.: US 8,829,455 B2
(45) Date of Patent: Sep. 9, 2014

(54) RADIOGRAPHIC IMAGING DEVICE

(71) Applicant: Fujifilm Corporation, Tokyo (JP)

(72) Inventors: Haruyasu Nakatsugawa, Kanagawa (JP); Yasunori Ohta, Kanagawa (JP); Naoyuki Nishino, Kanagawa (JP); Naoto Iwakiri, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/865,200

(22) Filed: Apr. 18, 2013

(65) Prior Publication Data

US 2013/0228694 A1  Sep. 5, 2013

Related U.S. Application Data

(63) Continuation of application No. PCT/JP2011/073965, filed on Oct. 18, 2011.

(30) Foreign Application Priority Data

Oct. 26, 2010 (JP) ................. 2010-240077

(51) Int. Cl.
*G01T 1/24* (2006.01)
*A61B 6/00* (2006.01)
*G03B 42/02* (2006.01)
*H04N 5/378* (2011.01)
*H04N 5/32* (2006.01)
*G03B 42/04* (2006.01)
*A61B 6/04* (2006.01)

(52) U.S. Cl.
CPC ............. *G01T 1/24* (2013.01); *A61B 6/4283* (2013.01); *G03B 42/02* (2013.01); *A61B 6/542* (2013.01); *A61B 6/4233* (2013.01); *H04N 5/378* (2013.01); *H04N 5/32* (2013.01); *A61B 6/56* (2013.01); *A61B 6/0407* (2013.01); *G01T 1/241* (2013.01); *G03B 42/04* (2013.01)
USPC ........................................... 250/370.09

(58) Field of Classification Search
CPC ........................................... G01T 1/241
USPC ................................. 250/370.08, 370.09
See application file for complete search history.

(56) References Cited

U.S. PATENT DOCUMENTS 5,751,783 A    5/1998  Granfors et al.
2001/0048080 A1*  12/2001  Meulenbrugge ......... 250/370.11

(Continued)

FOREIGN PATENT DOCUMENTS

JP    6-213677 A    8/1994
JP    07-201490 A    8/1995

(Continued)

OTHER PUBLICATIONS

Written Opinion of the ISA issued in International Application No. PCT/JP2011/073965 on Dec. 27, 2011.

(Continued)

*Primary Examiner* — David Porta
*Assistant Examiner* — Faye Boosalis
(74) *Attorney, Agent, or Firm* — SOLARIS Intellectual Property Group, PLLC

(57) ABSTRACT

A radiographic imaging device that may detect irradiation states of radiation is provided. Pixels for radiation detection that are provided in a radiation detector of an electronic cassette are configured with characteristics thereof being alterable. The characteristics are set in accordance with the imaging conditions of a radiation image by a cassette control section of the electronic cassette.

14 Claims, 16 Drawing Sheets

(56) References Cited

U.S. PATENT DOCUMENTS

| | | | |
|---|---|---|---|
| 2005/0200720 A1* | 9/2005 | Kameshima et al. | 348/220.1 |
| 2006/0071171 A1 | 4/2006 | Kameshima | |
| 2007/0280409 A1* | 12/2007 | Konno | 378/19 |
| 2009/0065702 A1 | 3/2009 | Kameshima et al. | |
| 2009/0086052 A1 | 4/2009 | Nakata et al. | |

FOREIGN PATENT DOCUMENTS

| | | |
|---|---|---|
| JP | H10-284289 | 10/1998 |
| JP | 2004-73256 | 3/2004 |
| JP | 2004-223157 A | 8/2004 |
| JP | 2005-253783 A | 9/2005 |
| JP | 2006-122667 A | 5/2006 |
| JP | 2007-54484 A | 3/2007 |
| JP | 2007-319199 A | 12/2007 |
| JP | 2009-98136 A | 5/2009 |
| JP | 2009-219538 A | 10/2009 |
| JP | 2010-136283 A | 6/2010 |

OTHER PUBLICATIONS

International Search Report issued in International Application No. PCT/JP2011/073965 on Dec. 27, 2011.

Office Action dated May 7, 2014 from the Japanese Patent Office in a Japanese patent application corresponding to the instant patent application.

* cited by examiner

■ : REGIONS OF ARRANGEMENT OF PIXELS FOR RADIATION DETECTION

INITIAL INFORMATION INPUT SCREEN

ENTER NAME OF SUBJECT, LOCATION TO BE IMAGED,
IMAGING POSTURE AND EXPOSURE CONDITIONS.

NAME:
LOCATION TO BE IMAGED
IMAGING POSTURE
EXPOSURE CONDITIONS
    TUBE VOLTAGE
    TUBE CURRENT

COMPLETE

RADIOGRAPHIC IMAGING DEVICE

CROSS-REFERENCE TO RELATED APPLICATIONS

This application is a continuation application of International Application No. PCT/JP2011/073965, filed Oct. 18, 2011, the disclosure of which is incorporated herein by reference in its entirety. Further, this application claims priority from Japanese Patent Application No. 2010-240077, filed Oct. 26, 2010, the disclosure of which is incorporated herein by reference in its entirety.

BACKGROUND

1. Technical Field

The present invention relates to a radiographic imaging device, and particularly relates to a radiographic imaging device that captures a radiation image expressed by radiation that has passed through an imaging target portion.

2. Related Art

In recent years, radiation detectors such as flat panel detectors (FPD) and the like have been realized. In an FPD, a radiation-sensitive layer is disposed on a thin film transistor (TFT) active matrix substrate, and the FPD is capable of converting radiation directly to digital data. A radiographic imaging device that uses this radiation detector to capture radiation images expressed by irradiated radiation has been realized. A system for converting radiation in the radiation detector used in this radiographic imaging device may be an indirect conversion system that first converts radiation to light using a scintillator and then converts the converted light to electronic charges in a semiconductor layer of photodiodes or the like, or a direct conversion system that converts radiation to electronic charges in a semiconductor layer of amorphous selenium or the like, or the like. Whatever the system, there are a variety of materials that may be used in a semiconductor layer.

In this kind of radiographic imaging device, the radiographic imaging device itself may be capable of detecting when an irradiation of radiation starts, detecting when an irradiation ends, and detecting a radiation amount and suchlike. If so, there is no need to connect the radiographic imaging device with a radiation source and with an imaging control device that collectively controls the radiographic imaging device and the radiation source or the like. This is preferable in that system structure may be simplified and control by an imaging control device may be simplified.

As a technology relating to this kind of radiographic imaging device that may detect radiation irradiation states, Japanese Patent Application Laid-Open (JP-A) No. 07-201490 discloses an X-ray diagnostics device equipped with an X-ray-to-light signals conversion unit and a light-to-electric signals conversion unit. The X-ray-to-light signals conversion unit converts X-rays to light signals. The light-to-electric signals conversion unit captures the light signals converted by the X-ray-to-light signals conversion unit with a plural number of pixels and converts the light signals to electric signals. This X-ray diagnostics device is equipped with an X-ray exposure amount control unit that controls X-ray exposure amounts in accordance with the electric signal values of a portion of the pixels of the light-to-electric signals conversion unit.

JP-A No. 2004-223157 discloses a radiation imaging device including a radiation detection section that detects a radiation image of a subject, and plural radiation amount detection sections that detect amounts of radiation from the imaging subject. This radiation imaging device includes a control section that, on the basis of a state of arrangement of the radiation imaging device, decides on a mode of use of outputs of the plural radiation amount detection sections.

JP-A No. 2007-54484 discloses a radiographic imaging device that includes a radiation conversion section, in which conversion elements are plurally arranged on a substrate, and a control unit. The conversion elements convert radiation irradiated from a radiation exposure unit directly or indirectly to electric signals. The conversion elements of the radiation conversion section are connected to signal lines, and the radiation conversion section outputs signals for generating an image. During radiation exposure by the radiation exposure unit, the control unit stops the radiation exposure by the radiation exposure unit on the basis of electric signals from one or more of the conversion elements.

However, in the technologies disclosed in the above-mentioned Patent Documents, although states of irradiation of radiation may be detected by the device itself, depending on the imaging conditions of a radiation image, radiation irradiation states may not necessarily always be detected.

For example, if a radiation image is captured in a state in which only a portion of an imaging region of the radiographic imaging device is used, because an imaging target portion is a leg area or an arm area or the like, imaging is usually performed in a state in which the imaging target portion is disposed at a central portion of the imaging region. Consequently, the levels of radiation amounts obtained by pixels for radiation detection that are provided in parts of the imaging region where the imaging target portion is not disposed differ greatly from the levels of radiation amounts obtained by pixels for radiation detection that are disposed in parts of the imaging region where the imaging target portion is disposed. Therefore, if the characteristics of the respective pixels for radiation detection are fixed in common, the radiation amounts at some of the pixels may saturate or the signal-to-noise ratio (SNR) of radiation amounts at the other pixels may be very low.

As another example, when videographic radiation images are captured, radiation amounts are smaller than when still images are captured. If the characteristics of pixels for radiation detection are fixed in common for video imaging and still imaging, radiation amounts in one may be saturated and/or radiation amounts in the other may have very low SNR values.

SUMMARY

The present invention has been made in order to solve the problem described above, and provides a radiographic imaging device that may more accurately detect radiation irradiation states.

A radiographic imaging device according to a first aspect of the present invention includes: a radiation detector provided with a plurality of radiation image acquisition pixels that are arranged in an array in an imaging region of a radiation image, the radiation image acquisition pixels acquiring image information representing the radiation image by respectively converting irradiated radiation to charges and accumulating the charges, and a plurality of radiation detection pixels that detect irradiated radiation by respectively converting irradiated radiation to charges and accumulating the charges, the radiation detection pixels being disposed in the imaging region and a characteristic of the radiation detection pixels being alterable; an acquisition unit that acquires an imaging condition of the radiation image; and a setting unit that sets the characteristic in accordance with the imaging condition acquired by the acquisition unit.

A program according to a tenth aspect of the present invention is a program to be executed by a radiographic imaging device including a radiation detector that is provided with a plurality of radiation image acquisition pixels that are arranged in an array in an imaging region of a radiation image, the radiation image acquisition pixels acquiring image information representing the radiation image by respectively converting irradiated radiation to charges and accumulating the charges, and a plurality of radiation detection pixels that detect irradiated radiation by respectively converting irradiated radiation to charges and accumulating the charges, the radiation detection pixels being disposed in the imaging region and a characteristic of the radiation detection pixels being alterable, wherein the program causes a computer to function as: an acquisition unit that acquires an imaging condition of the radiation image; and a setting unit that sets the characteristic in accordance with the imaging condition acquired by the acquisition unit.

A method according to an eleventh aspect of the present invention is a method for capturing a radiation image using a radiation detector that is provided with a plurality of radiation image acquisition pixels that are arranged in an array in an imaging region of a radiation image, the radiation image acquisition pixels acquiring image information representing the radiation image by respectively converting irradiated radiation to charges and accumulating the charges, and a plurality of radiation detection pixels that detect irradiated radiation by respectively converting irradiated radiation to charges and accumulating the charges, the radiation detection pixels being disposed in the imaging region and a characteristic of the radiation detection pixels being alterable, the method including: acquiring an imaging condition of the radiation image; and setting the characteristic in accordance with the acquired imaging condition.

BRIEF DESCRIPTION OF DRAWINGS

Exemplary embodiments of the present invention will be described in detail based on the following figures, wherein:

FIG. 12 is a schematic diagram showing an example of an initial information input screen in accordance with the exemplary embodiment.

DETAILED DESCRIPTION

Herebelow, modes for carrying out the present invention are described in detail with reference to the attached drawings. Herein, an example of a case in which the present invention is applied to a radiology information system, which is a system that collectively administers information managed by a radiology department in a hospital, is described.

Figure 1:
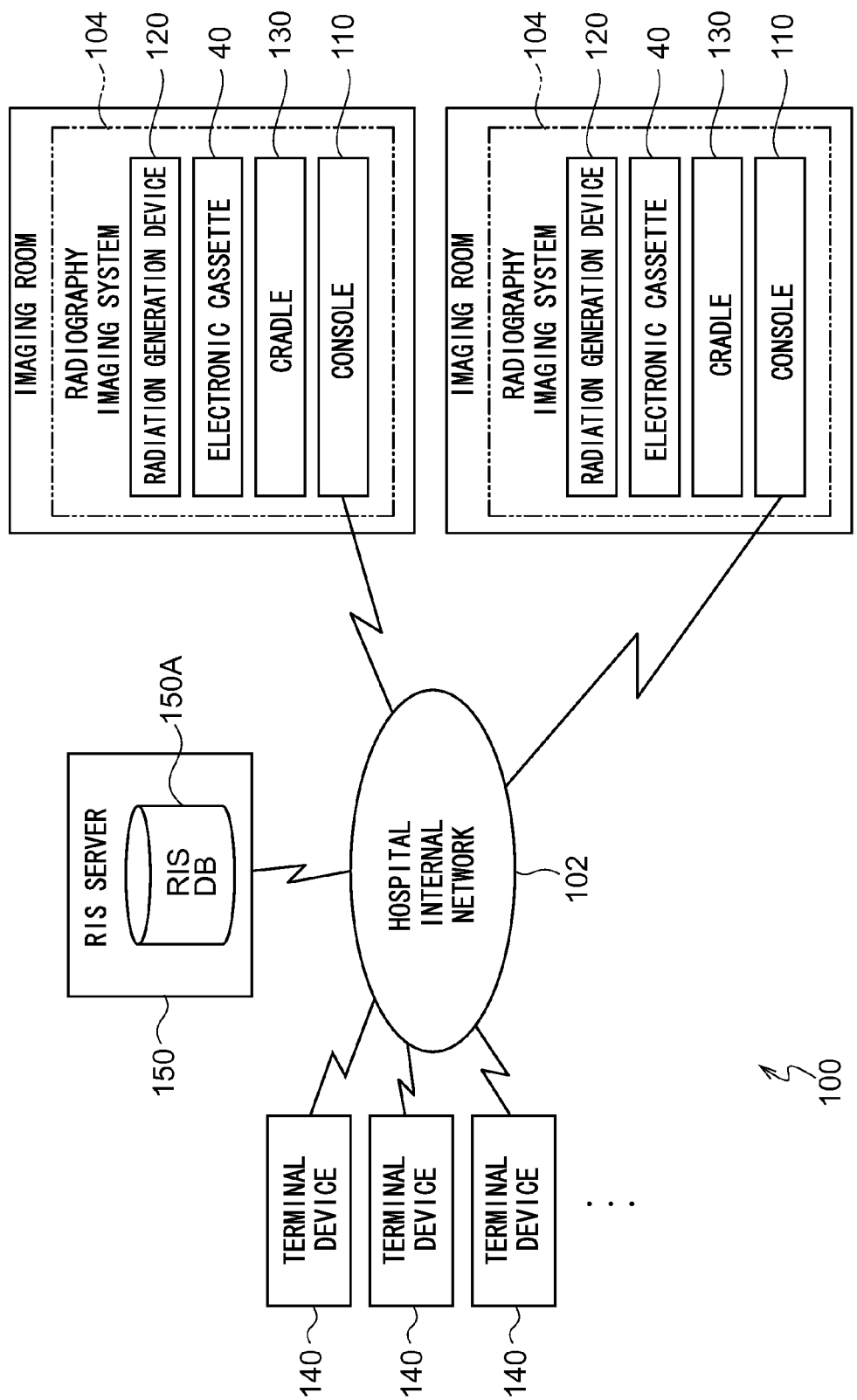
FIG. 1 is a block diagram illustrating the structure of a radiology information system in accordance with an exemplary embodiment.

First, the structure of a radiology information system (hereinafter referred to as an RIS) 100 according to the present exemplary embodiment is described with reference to FIG. 1.

The RIS 100 is a system for administering information of clinical appointments, medical records and so forth in the radiology department, and constitutes a portion of a hospital information system (hereinafter referred to as an HIS).

The RIS 100 is constituted with a plural number of imaging request terminal devices (hereinafter referred to as terminal devices) 140, an RIS server 150 and a radiation image capture system (hereinafter referred to as an imaging system) 104, which is separately installed in a radiography imaging room (or an operating room) in the hospital, being connected to a hospital internal network 102, which is formed with a wired and/or wireless local area network (LAN) or the like. Herein, the RIS 100 constitutes a portion of the HIS provided in the same hospital, and an HIS server (not shown in the drawings) that administers the HIS as a whole is also connected to the hospital internal network 102.

Each terminal device 140 is for a doctor, a radiographer or the like to input and monitor clinical information, facility reservations and the like. Imaging requests for radiation images, imaging bookings and the like are also conducted through the terminal device 140. The terminal device 140 includes a personal computer with a display device, and is connected with the RIS server 150 via the hospital internal network 102, enabling communications therebetween.

The RIS server 150 receives imaging requests from the terminal devices 140 and manages an imaging schedule for radiation images at the imaging system 104. The RIS server 150 contains a database 150A.

The database 150A is constituted to include: information relating to patients, such as information on attributes (name, gender, date of birth, age, blood type, body weight, a patient identification (ID) number and so forth) of each patient (imaging subject), medical record, treatment history, previously imaged radiation images, and the like; information relating to electronic cassettes 40 used in the imaging system 104 which are described below, such as an identification number (ID information) of each electronic cassette 40 and the type, size, sensitivity, the date of first use, the number of uses, and the like; and environmental information representing environments in which the electronic cassettes 40 are used to capture radiation images, which is to say environments in which the electronic cassettes 40 are employed (for example, a radiography imaging room, an operating room and the like).

The imaging system 104 carries out imaging of radiation images in response to instructions from the RIS server 150, in accordance with control by doctors, radiographers and the like. The imaging system 104 is equipped with a radiation generation device 120, which irradiates radiation X (see FIG. 7), constituted with radiation amounts depending on exposure conditions, from a radiation source 121 at an imaging subject (see FIG. 2). The imaging system 104 is also equipped with the electronic cassette 40, which incorporates a radiation detector 20 (see FIG. 7), a cradle 130, which charges a battery incorporated in the electronic cassette 40, and a console 110, which controls the electronic cassette 40 and the radiation generation device 120. The radiation detector 20 absorbs the radiation X that has passed through an imaging target portion of an imaging subject and generates electric charges and, on the basis of the generated charge amounts, generates image information representing a radiation image.

The console 110 acquires various kinds of information contained in the database 150A from the RIS server 150, stores the information in a hard disc drive (HDD) 116 (see FIG. 9), which is described below, and uses this information to control the electronic cassette 40 and the radiation generation device 120 in accordance with needs.

Figure 2:
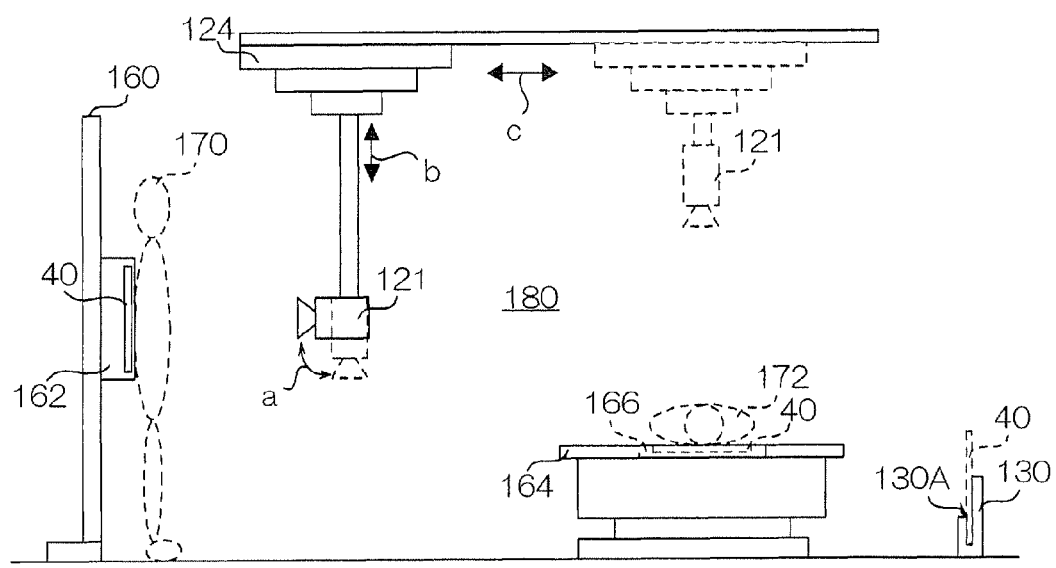
FIG. 2 is a side view showing an example of a state of arrangement of devices in a radiography imaging room of a radiation image capture system in accordance with the exemplary embodiment.

FIG. 2 shows an example of a state of arrangement of devices in a radiography imaging room 180 of the imaging system 104 in accordance with the present exemplary embodiment.

As shown in FIG. 2, in the radiography imaging room 180, a standing table 160 that is used when radiation imaging is being carried out on an imaging subject in a standing position and a reclining table 164 that is used when radiation imaging is being carried out on an imaging subject in a reclining position are provided. A space forward of the standing table 160 serves as an imaging position 170 of the imaging subject when radiation imaging is being carried out in the standing position, and a space above the reclining table 164 serves as an imaging position 172 of the imaging subject when radiation imaging is being carried out in the reclining position.

A retention portion 162 that retains the electronic cassette 40 is provided at the standing table 160. When a radiation image is being imaged in the standing position, the electronic cassette 40 is retained by the retention portion 162. Similarly, a retention portion 166 that retains the electronic cassette 40 is provided at the reclining table 164. When a radiation image is being imaged in the reclining position, the electronic cassette 40 is retained by the retention portion 166.

In the radiography imaging room 180, in order that both radiation imaging in the standing position and radiation imaging in the reclining position are possible with radiation from the single radiation source 121, a support and movement mechanism 124 is provided that supports the radiation source 121 to be turnable (in the direction of arrow a in FIG. 2) about a horizontal axis, movable in a vertical direction (the direction of arrow b in FIG. 2) and movable in a horizontal direction (the direction of arrow c in FIG. 2). The support and movement mechanism 124 is provided with each of a drive source that turns the radiation source 121 about the horizontal axis, a drive source that moves the radiation source 121 in the vertical direction and a drive source that moves the radiation source 121 in the horizontal direction (none of which are shown in the drawings).

In the cradle 130, an accommodation portion 130A capable of accommodating the electronic cassette 40 is formed.

When the electronic cassette 40 is accommodated in the accommodation portion 130A of the cradle 130, the battery incorporated in the electronic cassette 40 is charged up. When a radiation image is to be imaged, the electronic cassette 40 is taken from the cradle 130 by a radiographer or the like. If a posture for imaging is to be the standing position, the electronic cassette 40 is retained at the retention portion 162 of the standing table 160, and if the posture for imaging is to be the reclining position, the electronic cassette 40 is retained at the retention portion 166 of the reclining table 164.

In the imaging system 104 according to the present exemplary embodiment, various kinds of information are exchanged by wireless communications between the radiation generation device 120 and the console 110 and between the electronic cassette 40 and the console 110.

The electronic cassette 40 is not used only in conditions in which it is retained by the retention portion 162 of the standing table 160 or the retention portion 166 of the reclining table 164. The electronic cassette 40 is portable, and therefore may be used in conditions in which it is not retained at a retention portion, for imaging arm areas, leg areas and the like.

Figure 3:
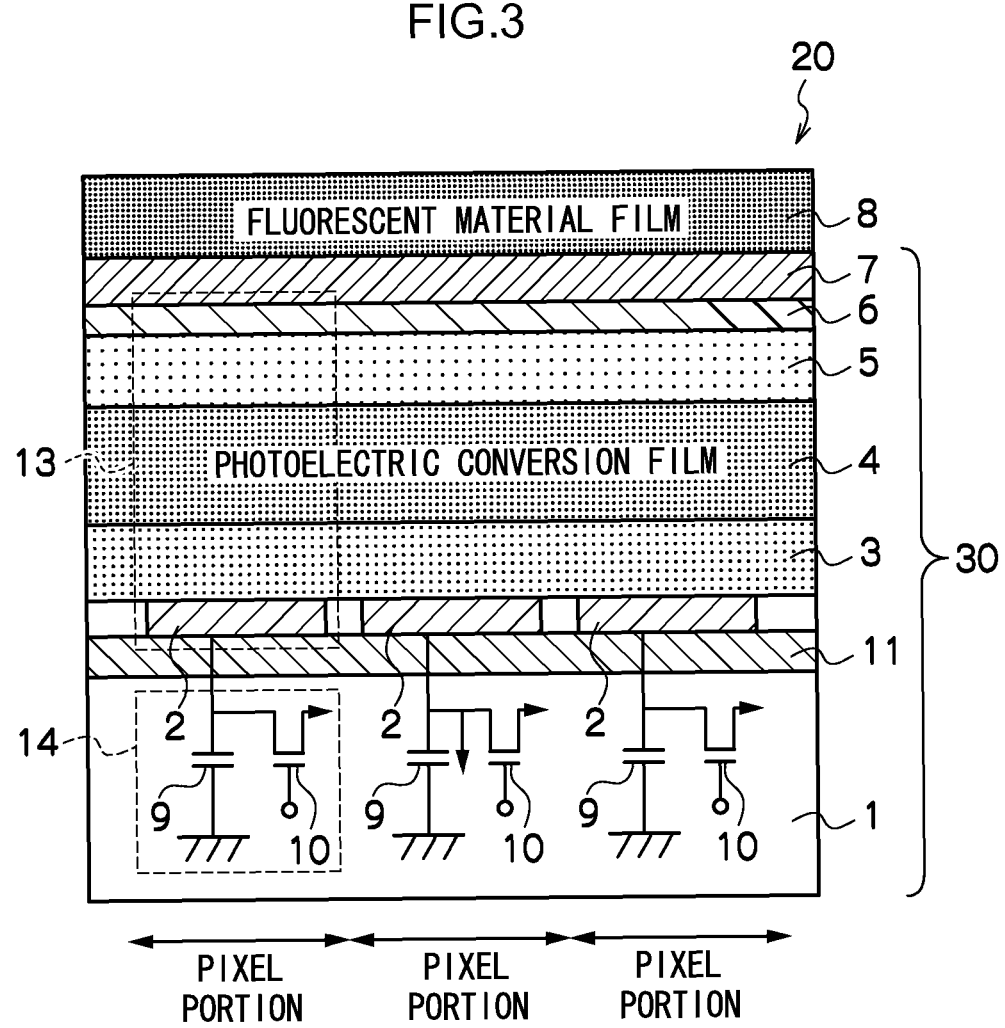
FIG. 3 is a sectional schematic diagram showing schematic structure of a three-pixel portion of a radiation detector in accordance with the exemplary embodiment.

Next, structures of the radiation detector 20 in accordance with the present exemplary embodiment are described. FIG. 3 is a sectional schematic diagram schematically showing the structure of a three-pixel portion of the radiation detector 20 in accordance with the present exemplary embodiment.

As shown in FIG. 3, in the radiation detector 20 according to the present exemplary embodiment, signal output portions 14, sensor portions 13 and a scintillator 8 are sequentially layered on an insulating substrate 1, and pixels are constituted by the signal output portions 14 and sensor portions 13. The pixels are plurally arrayed on the substrate 1 and, at each pixel, the signal output portion 14 and the sensor portion 13 are superposed.

The scintillator 8 is formed over the sensor portions 13 with a transparent insulating film 7 therebetween. The scintillator 8 is a film formed of a fluorescent material that converts radiation that is incident from above (the opposite side thereof from the side at which the substrate 1 is disposed) or below to light and emits the light. Because of the provision of the scintillator 8, radiation that has passed through an imaging subject is absorbed and light is emitted.

The wavelength range of the light emitted by the scintillator 8 is preferably in the visible light range (wavelengths from 360 nm to 830 nm). To enable monochrome imaging by the radiation detector 20, it is more preferable if a green wavelength range is included.

Specifically, if X-rays are used as the radiation and imaged, it is preferable if the fluorescent body used in the scintillator 8 includes cesium iodide (CsI). It is particularly preferable to use cesium iodide with thallium added thereto (CsI(Tl)), which has a light emission spectrum with a wavelength range of 420 nm to 700 nm when X-rays are irradiated thereon. CsI(Tl) has a light emission peak wavelength of 565 nm, in the visible light region. Gadolinium oxysulfide (GOS; $Gd_2O_2S:Tb$) or the like may also be used in the scintillator 8.

Each sensor portion 13 includes an upper electrode 6, a lower electrode 2, and a photoelectric conversion film 4 disposed between the upper and lower electrodes. The photoelectric conversion film 4 is constituted with an organic photoelectric conversion material that absorbs the light emitted by the scintillator 8 and generates charges.

Because the light produced by the scintillator 8 must be incident on the photoelectric conversion film 4, the upper electrode 6 is preferably constituted with a conductive material that is transparent at least to a wavelength of light emitted from the scintillator 8. Specifically, it is preferable to use transparent conducting oxides (TCO) which have high transparency to visible light and low resistance values. A thin metal film of gold or the like may be used as the upper electrode 6. However, if the transparency is to be 90% or above, the resistance value is likely to be high. Therefore, a TCO is more preferable. For example, ITO, IZO, AZO, FTO, $SnO_2$, $TiO_2$, $ZnO_2$ or the like may be preferably used. In regard to ease of processing, low resistance and transparency, ITO is the most preferable. Herein, the upper electrode 6 may be structured as a single common electrode for all pixels, or may be divided between the individual pixels.

The photoelectric conversion film 4 includes an organic photoelectric conversion material, absorbs light emitted from the scintillator 8, and generates electric charges in accordance with the absorbed light. If the photoelectric conversion film 4 includes this organic photoelectric conversion material, the film has a sharp absorption spectrum in the visible range and hardly any electromagnetic waves apart from the light emitted by the scintillator 8 are absorbed by the photoelectric conversion film 4. Thus, noise that is caused by light being emitted due to the absorption of radiation such as X-rays and the like at the photoelectric conversion film 4 may be effectively suppressed.

For the organic photoelectric conversion material constituting the photoelectric conversion film 4 to absorb the light emitted by the scintillator 8 most efficiently, it is preferable if the absorption peak wavelength of the organic photoelectric conversion material is as close as possible to the light emission peak wavelength of the scintillator 8. It is ideal if the absorption peak wavelength of the organic photoelectric conversion material and the light emission peak wavelength of the scintillator 8 match. However, provided a difference between the two is small, the light emitted from the scintillator 8 can be satisfactorily absorbed. In specific terms, it is preferable if a difference between the absorption peak wavelength of the organic photoelectric conversion material and the light emission peak wavelength of the scintillator 8 in response to the radiation is not more than 10 nm, and it is more preferable if the same is not more than 5 nm.

Organic photoelectric conversion materials that may satisfy these conditions include, for example, quinacridone-based organic compounds and phthalocyanine-based organic compounds. For example, an absorption peak wavelength of quinacridone in the visible region is 560 nm. Therefore, if quinacridone is used as the organic photoelectric conversion material and CsI(Tl) is used as the material of the scintillator 8, the difference between the peak wavelengths may be kept to within 5 nm, and charge amounts generated in the photoelectric conversion film 4 may be substantially maximized. Even if GOS:Tb is used as the material of the scintillator 8, the difference between the peak wavelengths may be kept to around 10 nm, and charge amounts generated in the photoelectric conversion film 4 may be substantially maximized.

Next, the photoelectric conversion film 4 that is applicable to the radiation detector 20 according to the present exemplary embodiment is described in concrete terms.

Each electromagnetic wave absorption/photoelectric conversion portion of the radiation detector 20 according to the present exemplary embodiment may be structured by the pair of electrodes 2 and 6 and an organic layer including the photoelectric conversion film 4 sandwiched between the pair of electrodes 2 and 6. In more specific terms, this organic layer may be formed by laminating or mixing a portion that absorbs electromagnetic waves, a photoelectric conversion portion, an electron transport portion, a hole transport portion, an electron blocking portion, a hole blocking portion, a crystallization prevention portion, an electrode and an interlayer contact improvement portion, or the like.

The organic layer preferably includes an organic p-type compound or an organic n-type compound.

The term "organic p-type semiconductor" (or compound) as used here means a donor organic semiconductor (compound) that has the characteristic of easily donating electrons, principally typified by hole-transporting organic compounds. More specifically, this refers to the organic compound with the smaller ionization potential when two organic materials are used in contact with one another. Thus, any organic compound may be used as the donor organic compound provided that organic compound donates electrons.

The term "organic n-type semiconductor" (or compound) as used here means an acceptor organic semiconductor (compound) that has the characteristic of easily accepting electrons, principally typified by electron-transporting organic compounds. More specifically, this refers to the organic compound with the larger electron affinity when two organic materials are used in contact with one another. Thus, any organic compound may be used as the acceptor organic compound provided that organic compound accepts electrons.

Materials that may be used as the organic p-type semiconductor and the organic n-type semiconductor and the structure of the photoelectric conversion film 4 are described in detail in JP-A No. 2009-32854, so are not described here. Note that the photoelectric conversion film 4 may be formed to further include fullerenes or carbon nanotubes.

In regard to absorbing light from the scintillator 8, it is preferable if the thickness of the photoelectric conversion film 4 is a film thickness as thick as possible. However, beyond a certain level of thickness, the strength of an electric field that is produced in the photoelectric conversion film 4 by a bias voltage applied from the two sides of the photoelectric conversion film 4 is weakened and charges may not be collected. Therefore, a thickness from 30 nm to 300 nm is preferable, a thickness from 50 nm to 250 nm is more preferable, and a thickness from 80 nm to 200 nm is particularly preferable.

In the radiation detector 20 shown in FIG. 3, the photoelectric conversion film 4 is a single structure common to all pixels. However, the photoelectric conversion film 4 may be divided between the respective pixels.

The lower electrode 2 is a thin film that is divided between the respective pixels. The lower electrode 2 may be constituted with a transparent or non-transparent conductive material; aluminium, silver or the like may be favorably used.

The thickness of the lower electrode 2 may be set in a range, for example, from 30 nm to 300 nm.

In each sensor portion 13, a predetermined bias voltage is applied between the upper electrode 6 and the lower electrode 2. Thus, one type of the charges (holes and electrons) produced in the photoelectric conversion film 4 may be made to migrate to the upper electrode 6 and the other type may be made to migrate to the lower electrode 2. In the radiation detector 20 according to the present exemplary embodiment, wiring is connected to the upper electrode 6 and the bias voltage is applied to the upper electrode 6 via this wiring. The polarity of the bias voltage is set such that the electrons produced in the photoelectric conversion film 4 migrate to the upper electrode 6 and the holes migrate to the lower electrode 2. However, the polarity may be the opposite.

It is sufficient if the sensor portion 13 structuring each pixel includes at least the lower electrode 2, the photoelectric conversion film 4 and the upper electrode 6. However, to suppress an increase in dark current, it is preferable to provide one or other of an electron blocking film 3 and a hole blocking film 5, and it is more preferable to provide both.

The electron blocking film 3 may be provided between the lower electrode 2 and the photoelectric conversion film 4. When the bias voltage is applied between the lower electrode 2 and the upper electrode 6, electrons are injected from the lower electrode 2 to the photoelectric conversion film 4. Thus, an increase in the dark current may be suppressed.

An organic material with electron affinity may be used for the electron blocking film 3.

A material that is used for the electron blocking film 3 in practice may be selected in accordance with the material of the adjacent electrode, the material of the adjacent photoelectric conversion film 4, and the like. It is preferable that the electron affinity (Ea) be at least 1.3 eV greater than the work function (Wf) of the material of the adjacent electrode, and that the ionization potential (Ip) be the same as or smaller than the ionization potential of the material of the adjacent photoelectric conversion film 4. Materials that may be employed as this organic material with electron affinity are described in detail in JP-A No. 2009-32854, so are not described here.

To reliably express the dark current suppression effect and avoid a reduction in photoelectric conversion efficiency of the sensor portion 13, the thickness of the electron blocking film 3 is preferably from 10 nm to 200 nm, is more preferably from 30 nm to 150 nm, and is particularly preferably from 50 nm to 100 nm.

The hole blocking film 5 may be provided between the photoelectric conversion film 4 and the upper electrode 6. When the bias voltage is applied between the lower electrode 2 and the upper electrode 6, holes are injected from the upper electrode 6 to the photoelectric conversion film 4. Thus, an increase in the dark current may be suppressed.

An organic material with electron acceptance may be used for the hole blocking film 5.

To reliably express the dark current suppression effect and avoid a reduction in photoelectric conversion efficiency of the sensor portion 13, the thickness of the hole blocking film 5 is preferably from 10 nm to 200 nm, is more preferably from 30 nm to 150 nm, and is particularly preferably from 50 nm to 100 nm.

A material that is used for the hole blocking film 5 in practice may be selected in accordance with the material of the adjacent electrode, the material of the adjacent photoelectric conversion film 4, and the like. It is preferable that the ionization potential (Ip) be at least 1.3 eV greater than the work function (Wf) of the material of the adjacent electrode, and that the electron affinity (Ea) be the same as or larger than the electron affinity of the material of the adjacent photoelectric conversion film 4. Materials that may be employed as this organic material with electron acceptance are described in detail in JP-A No. 2009-32854, so are not described here.

If the bias voltage is set such that, of the charges produced in the photoelectric conversion film 4, the holes migrate to the upper electrode 6 and the electrons migrate to the lower electrode 2, it is sufficient to exchange the positions of the electron blocking film 3 and the hole blocking film 5. It may be that neither of the electron blocking film 3 and the hole blocking film 5 is provided, but the dark current suppression effect may be obtained to some extent if one or the other is provided.

The signal output portion 14 is formed at the surface of the insulating substrate 1 under the lower electrode 2 of each pixel. The structure of the signal output portion 14 is schematically illustrated in FIG. 4.

Figure 4:
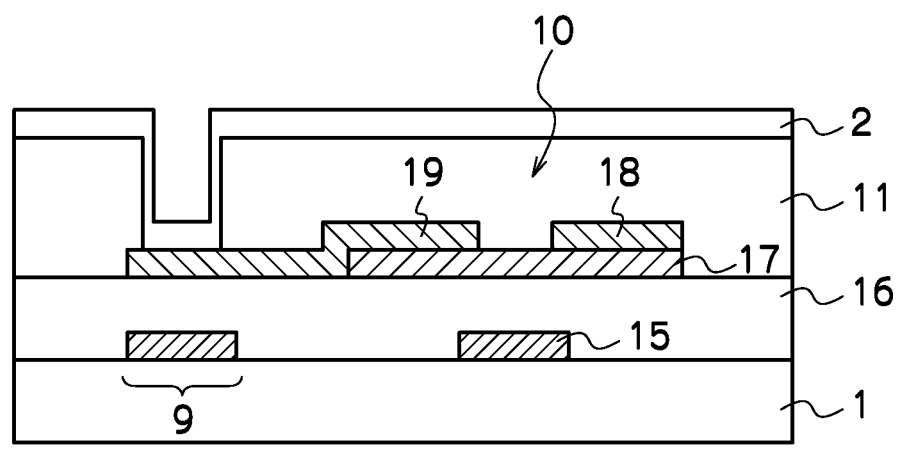
FIG. 4 is a sectional side diagram schematically showing the structure of a signal output portion of a one-pixel portion of the radiation detector in accordance with the exemplary embodiment.

As shown in FIG. 4, each signal output portion 14 according to the present exemplary embodiment is formed with a capacitor 9, which corresponds with the lower electrode 2 and accumulates charges that have migrated to the lower electrode 2, and a field effect-type thin film transistor (which may hereinafter be referred to simply as a thin film transistor) 10, which converts the charges accumulated at the capacitor 9 to electronic signals and outputs the electronic signals. A region in which the capacitor 9 and the thin film transistor 10 are formed includes a region that overlaps with the lower electrode 2 in plan view. Because of this structure, the signal output portion 14 and the sensor portion 13 of each pixel are superposed in the thickness direction. To minimize a planar area of the radiation detector 20 (the pixels), it is desirable if the region in which each capacitor 9 and thin film transistor 10 are formed is completely covered by the lower electrode 2.

An insulating film 11 is provided between the substrate 1 and the lower electrode 2. The capacitor 9 is electrically connected with the corresponding lower electrode 2 via wiring of a conductive material that is formed to penetrate through the insulating film 11. Thus, charges collected by the lower electrode 2 may be allowed to migrate to the capacitor 9.

In each thin film transistor 10, a gate electrode 15, a gate insulation film 16 and an active layer (a channel layer) 17 are layered. A source electrode 18 and a drain electrode 19 are formed, with a predetermined gap formed therebetween, on the active layer 17.

The active layer 17 may be formed of, for example, amorphous silicon, a non-crystalline oxide, an organic semiconductor material, carbon nanotubes or the like. The material structuring the active layer 17 is not limited to these.

A non-crystalline oxide structuring the active layer 17 is preferably an oxide containing at least one of indium, gallium and zinc (for example, an In—O material). It is more preferable if the oxide contains at least two of indium, gallium and zinc (for example, an In—Zn—O material, an In—Ga—O material or a Ga—Zn—O material), and particularly preferable if the oxide contains indium, gallium and zinc. An In—Ga—Zn—O non-crystalline oxide is preferably a non-crystalline oxide whose composition in a crystalline state would be represented by $InGaO_3(ZnO)m$ (m being a natural number that is less than 6), and is particularly preferably $InGaZnO_4$.

Organic semiconductor materials that may structure the active layer 17 include phthalocyanine compounds, pentacene, vanadyl phthalocyanine and the like. However, this is not limiting. The structures of phthalocyanine compounds are described in detail in JP-A No. 2009-212389, so are not described here.

If the active layer 17 of the thin film transistor 10 is formed with a non-crystalline oxide, an organic semiconductor material or carbon nanotubes, the active layer 17 does not absorb radiation such as X-rays and the like, or absorbs the same only in very small amounts. Therefore, the generation of noise in the signal output portion 14 may be effectively suppressed.

If the active layer 17 is formed of carbon nanotubes, the switching speed of the thin film transistor 10 may be increased, and the thin film transistor 10 may be formed to have a low level of absorption of light in the visible region. In a case in which the active layer 17 is formed of carbon nanotubes, the performance of the thin film transistor 10 is greatly reduced if trace amounts of metal impurities are mixed into the active layer 17. Therefore, it is necessary to separate and extract carbon nanotubes with very high purity by centrifugal separation or the like before forming this active layer 17.

Film formation at low temperatures is possible for both the non-crystalline oxide, organic semiconductor material or carbon nanotubes constituting the active layer 17 of the thin film transistor 10 and the organic photoelectric conversion material constituting the photoelectric conversion film 4. Accordingly, the insulating substrate 1 is not limited to being a substrate with a high heat resistance, such as a semiconductor substrate, a quartz substrate, a glass substrate or the like. A flexible substrate of a plastic or the like, or a substrate using an aramid, bionanofibers or the like may be employed. Specifically, a flexible substrate of a polyester such as polyethylene terephthalate, polybutylene phthalate, polyethylene naphthalate or the like, or a polystyrene, polycarbonate, polyether sulfone, polyarylate, polyimide, polycycloolefin, norbornene resin, poly(chlorotrifluoroethylene) or the like may be used. If a flexible substrate made of such a plastic is used, a reduction in weight is possible, which enhances portability for, for example, carrying and the like.

On the insulating substrate 1, the following layers may be provided: an insulating layer for ensuring insulation; a gas barrier layer for preventing permeation of moisture, oxygen and the like; an undercoating layer for improving flatness and contact with the electrodes and the like; and so forth.

In the case of an aramid, a transparent electrode material may be cured at a high temperature and lowered in resistance in order for a high-temperature process with a temperature of 200° C. or above to be employable. An automatic driver chip mounting process including a solder reflow process is also applicable. Because the thermal expansion coefficient of ITO or glass plate or the like is low, there is little warping of the aramid after the completion of fabrication, and the aramid is unlikely to break. The aramid may form a thinner substrate than a glass substrate or the like. A structure in which an aramid is laminated with an ultra-thin glass plate may also be formed.

Bionanofibers are a composite of a transparent resin with cellulose microfibril strands (bacterial cellulose) produced from a bacteria (an acetobacter such as *Acetobacter Xylinum*). The cellulose microfibril strands have widths of 50 nm, one tenth of the wavelengths of visible light, and have high strength, high resilience and low thermal expansion. The bacterial cellulose is immersed in a transparent resin such as an acrylic resin, an epoxy resin or the like, and the resin is cured. Thus, bionanofibers can be provided that contain 60-70% fibers and exhibit a transparency of about 90% for a wavelength of 500 nm. The bionanofibers have a low thermal expansion coefficient (3 to 7 ppm) compared with silicon crystal, have a strength comparable with steel (460 MPa) and a high resilience (30 GPa), and are flexible. Therefore, the insulating substrate 1 may be made thinner than one formed from a glass plate or the like.

In the present exemplary embodiment, a TFT substrate 30 is formed on the substrate 1 by sequential formation of the signal output portions 14, the sensor portions 13 and the transparent insulating film 7. The radiation detector 20 is then formed by the scintillator 8 being adhered onto the TFT substrate 30 using an adhesive resin or suchlike with low light absorption.

Figure 5:
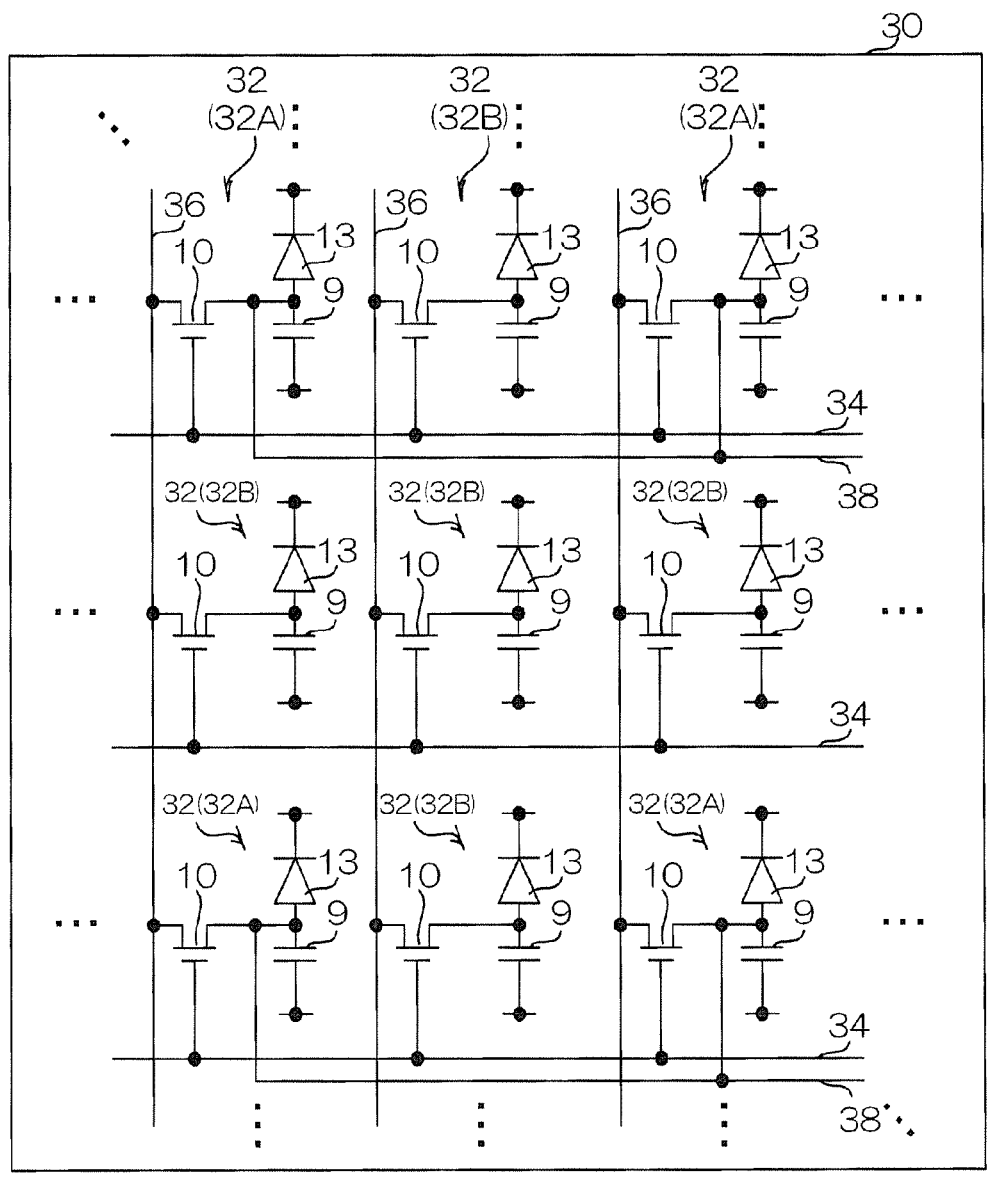
FIG. 5 is a plan diagram showing structures of a radiation detector in accordance with the exemplary embodiment.

As shown in FIG. 5, pixels 32 are plurally provided in two dimensions on the TFT substrate 30, in a certain direction (a row direction in FIG. 5), and a direction orthogonal to the certain direction (a column direction in FIG. 5). Each pixel 32 is structured to include the above-described sensor portion 13, capacitor 9 and thin film transistor 10.

Plural gate lines 34 and plural data lines 36 are provided in the radiation detector 20. The gate lines 34 extend in the certain direction (the row direction) and are for turning the thin film transistors 10 on and off. The data lines 36 extend in the orthogonal direction (the column direction) and are for reading out charges via the thin film transistors 10 that have been turned on.

The radiation detector 20 has a flat-plate form, and is formed in a quadrilateral shape with four outer edges in plan view, and more specifically a rectangular shape.

In the radiation detector 20 according to the present exemplary embodiment, some of the pixels 32 are used for detecting radiation irradiation states, and a radiation image is captured by the rest of the pixels 32. Hereinafter, the pixels 32 for detecting radiation irradiation states are referred to as radiation detection pixels 32A, and the other pixels 32 are referred to as radiation image acquisition pixels 32B.

In the radiation detector 20 according to the present exemplary embodiment, because a radiation image is captured by the radiation image acquisition pixels 32B of the pixels 32 excluding the radiation detection pixels 32A, pixel information of the radiation image may not be acquired for the positions at which the radiation detection pixels 32A are disposed. Accordingly, the radiation detection pixels 32A are disposed so as to be scattered in the radiation detector 20 according to the present exemplary embodiment, and missing pixel correction processing is executed by the console 110. The missing pixel correction processing generates pixel information of the radiation image for each position at which a radiation detection pixel 32A is disposed by interpolation using image information acquired by the radiation image acquisition pixels 32B disposed around that radiation detection pixel 32A.

In the imaging system 104 according to the present exemplary embodiment, imaging is carried out in a state in which the measurement target portion is disposed at least at a central portion of the imaging region, both when imaging is carried out using the whole area of the imaging region of the radiation detector 20, such as when the imaging target portion is a torso area or the like, and when imaging is carried out using only a portion of the imaging region of the radiation detector 20, such as when the imaging target portion is a leg area, an arm area, a hand area or the like.

In the radiation detector 20 according to the present exemplary embodiment, as is schematically illustrated by the example in FIG. 6, the radiation detection pixels 32A are disposed at regions in the vicinity of the central portion of the imaging region of the radiation detector 20 (which are hereinafter referred to as central detection regions), and at regions in vicinities of the four corners of a peripheral edge of the imaging region (which are hereinafter referred to as peripheral edge detection regions).

To detect radiation irradiation states, the electronic cassette 40 according to the present exemplary embodiment is provided with a radiation amount acquisition function that acquires information representing irradiation amounts of the radiation X from the radiation source 121 (hereinafter referred to as "radiation amount information").

Accordingly, in the radiation detector 20 according to the present exemplary embodiment, as shown in FIG. 5, direct connection readout wires 38 are separately provided extending in the certain direction (the row direction) from each of the radiation detection pixels 32A. Each direct connection readout wire 38 is connected with a portion that connects between the capacitor 9 and the thin film transistor 10 in the radiation detection pixel 32A, and the direct connection readout wire 38 is for directly reading out charges accumulated in the capacitor 9. In the radiation detector 20 according to the present exemplary embodiment, a single direct connection readout wire 38 is assigned to a plural number of the radiation detection pixels 32A that are lined up in the certain direction. Thus, the portions connecting between the capacitors 9 and thin film transistors 10 in the plural number of radiation detection pixels 32A are connected to a common (single) direct connection readout wire 38.

Figure 7:
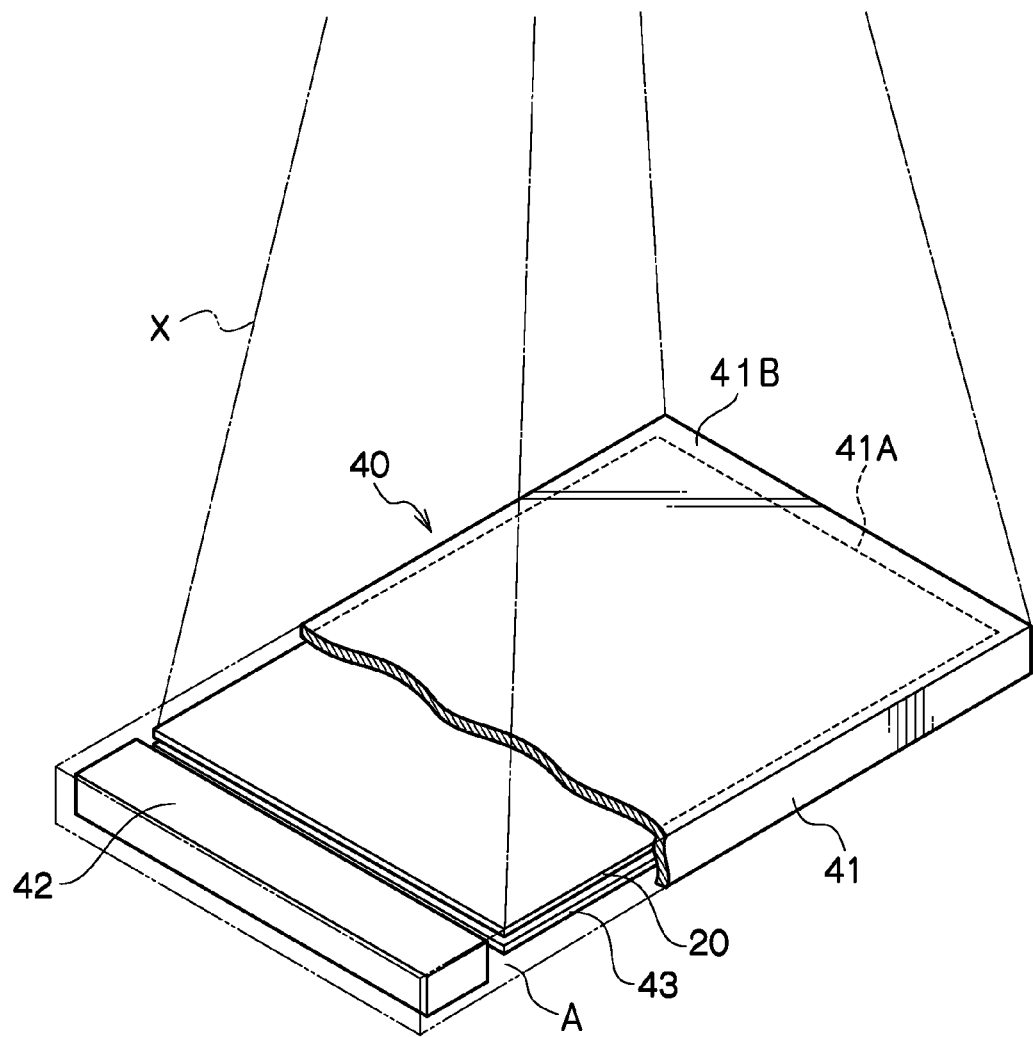
FIG. 7 is a perspective view showing structures of an electronic cassette in accordance with the exemplary embodiment.

Next, the structure of the electronic cassette 40 according to the present exemplary embodiment is described. FIG. 7 shows a perspective view illustrating structures of the electronic cassette 40 in accordance with the present exemplary embodiment.

As shown in FIG. 7, the electronic cassette 40 according to the present exemplary embodiment is provided with a casing 41 formed of a material that transmits the radiation, and the electronic cassette 40 is structured to be waterproof and tightly sealed. During use in an operating room or the like, blood and saprophytic bacteria and the like may adhere to the electronic cassette 40. Accordingly, the electronic cassette 40, being structured to be waterproof and tightly sealed, is washed with disinfectant as required. Thus, the individual electronic cassettes 40 may be used repeatedly.

A space A that accommodates various components is formed inside the casing 41. Inside the space A, the radiation detector 20 that detects radiation X passing through the imaging subject and a lead plate 43 that absorbs back scattering of the radiation X are arranged in this order from an irradiated surface side of the casing 41 on which the radiation X is irradiated.

In the electronic cassette 40 according to the present exemplary embodiment, a region of one face of the flat plate-shaped casing 41 that corresponds to positions at which the radiation detector 20 is disposed is a quadrilateral imaging region 41A at which the radiation X can be detected. A face of the casing 41 that includes the imaging region 41A is a top plate 41B of the electronic cassette 40. In the electronic cassette 40 according to the present exemplary embodiment, the radiation detector 20 is disposed such that the TFT substrate 30 is at the top plate 41B side of the radiation detector 20, and the radiation detector 20 is adhered to the face of the top plate 41B at the inner side of the casing 41 (i.e., the face of the top plate 41B that is at the opposite side thereof from the face on which the radiation is incident)

As shown in FIG. 7, a case 42 is disposed at one end of the interior of the casing 41. The case 42 accommodates a cassette control section 58 and a power supply section 70 (both shown in FIG. 9), which are described below, at a location that does not overlap with the radiation detector 20 (is outside the extent of the imaging region 41A).

To reduce the overall weight of the electronic cassette 40, the casing 41 is constituted of, for example, carbon fiber (carbon fibers), aluminium, magnesium, bionanofibers (cellulose microfibrils), or a compound material or the like.

As a compound material, for example, a material including reinforced fiber resin is used. A reinforced fiber resin contains carbon, cellulose or the like. Specifically, carbon fiber reinforced plastic (CFRP), a structure in which a foam material is sandwiched by CFRP, or a structure in which CFRP is coated onto surfaces of a foam material, or the like can be used as a composite material. In the present exemplary embodiment, a structure in which a foam material is sandwiched by CFRP is used. Thus, the strength (rigidity) of the casing 41 may be made higher than if the casing 41 is structured of carbon alone.

Figure 8:
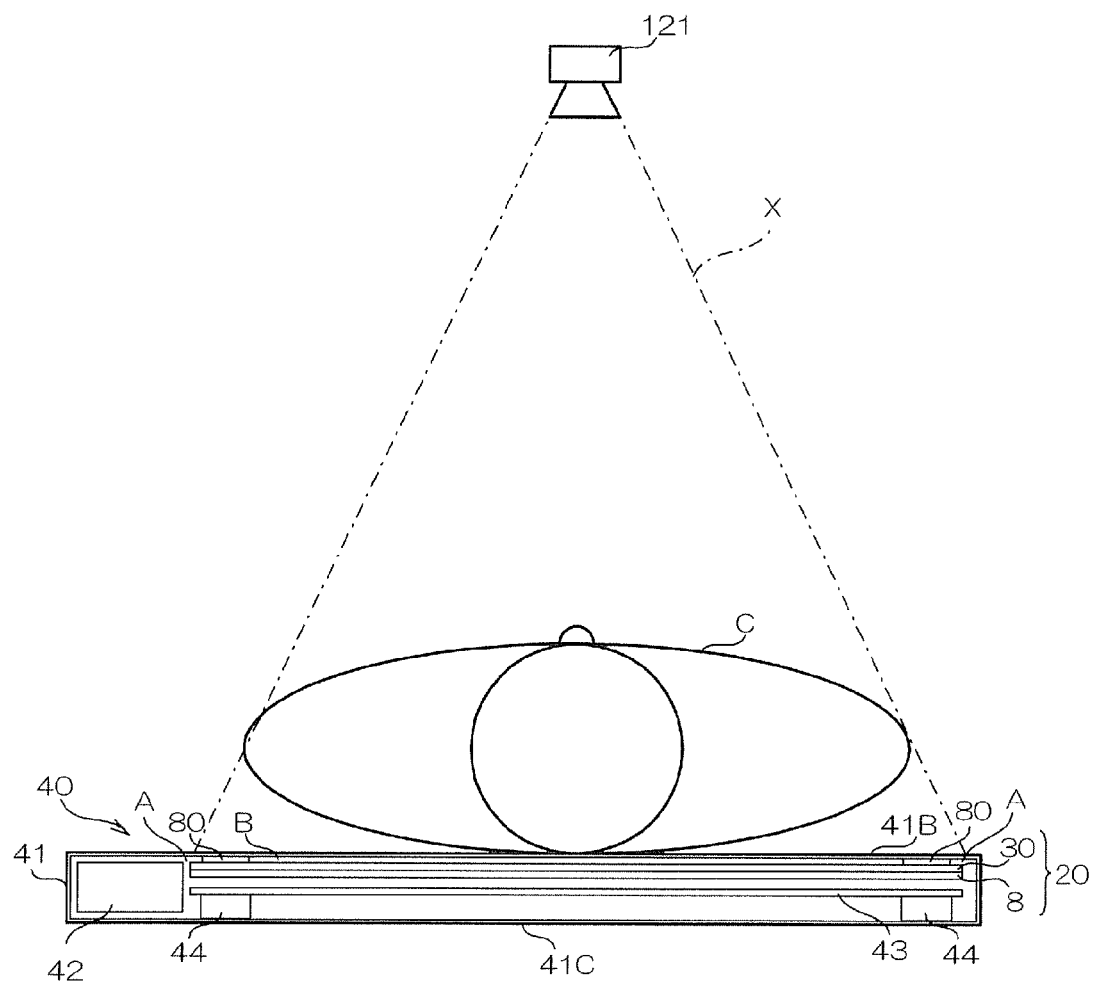
FIG. 8 is a sectional side diagram showing the structures of the electronic cassette in accordance with the exemplary embodiment.

As shown in FIG. 8, a support body 44 is disposed inside the casing 41 at the inner face of a rear face portion 41C, which opposes the top plate 41B. Between the support body 44 and the top plate 41B, the radiation detector 20 and the lead plate 43 are arranged in this order in the direction of irradiation of the radiation X. With a view to weight reduction and tolerating dimensional variations, the support body 44 is structured of, for example, a foam material. The support body 44 supports the lead plate 43.

As is also shown in FIG. 8, an adhesion member 80 is provided that separably adheres the TFT substrate 30 of the radiation detector 20 to the inner side of the top plate 41B. As the adhesion member 80, for example, double-sided tape can be used. In this case, the double-sided tape is formed such that the adhesive strength of one adhesion face is stronger than the adhesive strength of the other adhesion face.

Specifically, the face with the weaker adhesion strength (a weak adhesion face) is specified to have a 180°-peel adhesion strength of not more than 1.0 N/cm. The face with the stronger adhesion strength (a strong adhesion face) is applied to the top plate 41B, and the weak adhesion face is applied to the TFT substrate 30. Thus, the thickness of the electronic cassette 40 may be made thinner than if the radiation detector 20 were fixed to the top plate 41B by fixing members such as screws or the like. In addition, if an impact or load deforms the top plate 41B, the radiation detector 20 follows the deformation of the high-stiffness top plate 41B, and only large curvatures (gentle curves) are produced. Thus, the possibility of the radiation detector 20 breaking due to tight local curvatures is reduced. Furthermore, the radiation detector 20 contributes to an increase in stiffness of the top plate 41B.

Thus, in the electronic cassette 40 according to the present exemplary embodiment, the radiation detector 20 is adhered to an interior portion of the top plate 41B of the casing 41. Accordingly, the casing 41 is configured to be dividable in two, between the top plate 41B side and the rear face portion 41C side. Hence, when the radiation detector 20 is to be adhered to the top plate 41B or the radiation detector 20 is to be peeled from the top plate 41B, the casing 41 is put into the state that is divided in two between the top plate 41B side and the rear face portion 41C side.

In the present exemplary embodiment, adhesion of the radiation detector 20 to the top plate 41B need not be performed in a clean room or the like. This is because, if contaminants such as metal scraps or the like that absorb radiation are trapped between the radiation detector 20 and the top plate 41B, the radiation detector 20 may be peeled from the top plate 41B and these contaminants may be removed.

Now, principal structures of an electronic system of the imaging system 104 in accordance with the present exemplary embodiment are described with reference to FIG. 9.

Figure 9:
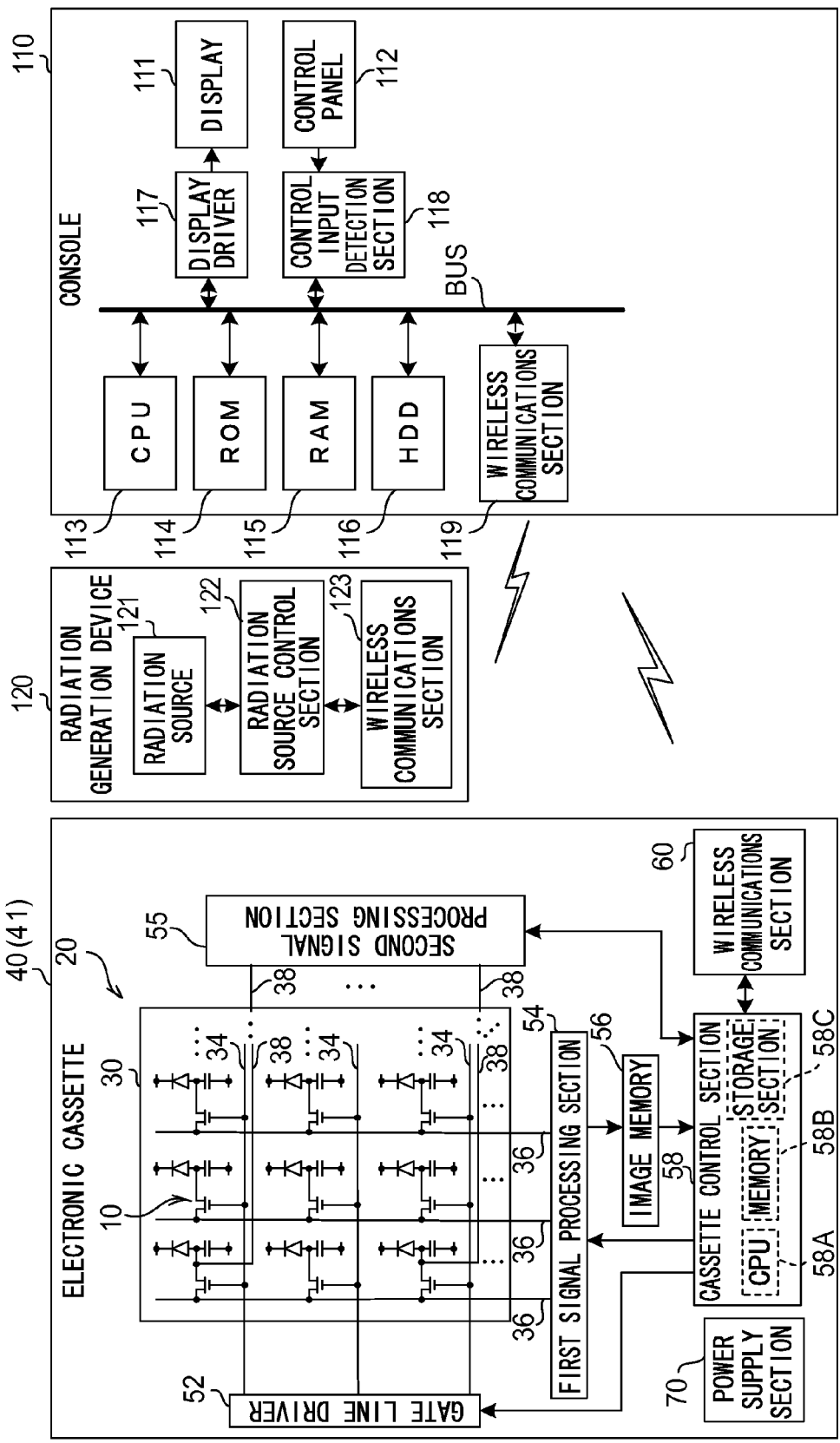
FIG. 9 is a block diagram showing the principal structures of an electronic system of the radiation image capture system in accordance with the exemplary embodiment.

As shown in FIG. 9, the radiation detector 20 incorporated in the electronic cassette 40 is provided with a gate line driver 52, which is disposed at one of two adjoining sides of the radiation detector 20, and a first signal processing section 54, which is disposed at the other of the two adjoining sides. The individual gate lines 34 of the TFT substrate 30 are connected to the gate line driver 52, and the individual data lines 36 of the TFT substrate 30 are connected to the first signal processing section 54.

An image memory 56, the cassette control section 58 and a wireless communications section 60 are also provided inside the casing 41.

The thin film transistors 10 of the TFT substrate 30 are sequentially turned on in row units by signals provided from the gate line driver 52 via the gate lines 34, and charges that are read out by the thin film transistors 10 that have been turned on are propagated through the data lines 36 as electronic signals and inputted to the first signal processing section 54. Thus, the charges are sequentially read out row by row, and a two-dimensional radiation image may be acquired.

Although not shown in the drawings, the first signal processing section 54 is provided with an amplification circuit and a sample and hold circuit for each of the individual data lines 36. The amplification circuits amplify the inputted electronic signals. The electronic signals that have been propagated through the respective data lines 36 are amplified by the amplification circuits and then retained in the sample and hold circuits. At the output side of the sample and hold circuits, a multiplexer and an analog-to-digital (A/D) converter are connected in this order. The electronic signals retained at the respective sample and hold circuits are sequentially (serially) inputted to the multiplexer, and are converted to digital image data by the A/D converter.

The image memory 56 is connected to the first signal processing section 54, and the image data outputted from the A/D converter of the first signal processing section 54 is sequentially stored in the image memory 56. The image memory 56 has a storage capacity capable of storing a predetermined number of frames of image data. Each time a radiation image is captured, image data obtained by the imaging is sequentially stored in the image memory 56.

The image memory 56 is connected to the cassette control section 58. The cassette control section 58 includes a microcomputer, and is provided with a central processing unit (CPU) 58A, a memory 58B including a read-only memory (ROM) and random access memory (RAM), and a non-volatile storage section 58C formed of flash memory or the like. The cassette control section 58 controls overall operations of the electronic cassette 40.

The wireless communications section 60 is connected to the cassette control section 58. The wireless communications section 60 complies with wireless LAN (local area network) standards, typically IEEE (Institute of Electrical and Electronics Engineers) standards 802.11a/b/g and the like. The wireless communications section 60 controls transfers of various kinds of information between the cassette control section 58 and external equipment by wireless communications. The cassette control section 58 is capable of wireless communications, via the wireless communications section 60, with external devices such as the console 110 that controls the capture of radiation images and the like, and may exchange various kinds of information with the console 110 and the like.

The electronic cassette 40 is also provided with the power supply section 70. The various circuits and components mentioned above (the gate line driver 52, the first signal processing section 54, the image memory 56, the wireless communications section 60, the microcomputer that functions as the cassette control section 58, and the like) are driven by electrical power supplied from the power supply section 70. The power supply section 70 incorporates a battery (a rechargeable secondary cell), so as not to impede portability of the electronic cassette 40, and supplies power to the various circuits and components from the charged battery. Wiring connecting the power supply section 70 with the various circuits and components is not shown in FIG. 9.

The radiation detector 20 according to the present exemplary embodiment is also provided with a second signal processing section 55 for implementing the above-mentioned radiation amount acquisition function, at the opposite side of the TFT substrate 30 from the side thereof at which the gate line driver 52 is disposed. The individual direct connection readout wires 38 of the TFT substrate 30 are connected to the second signal processing section 55.

Figure 10:
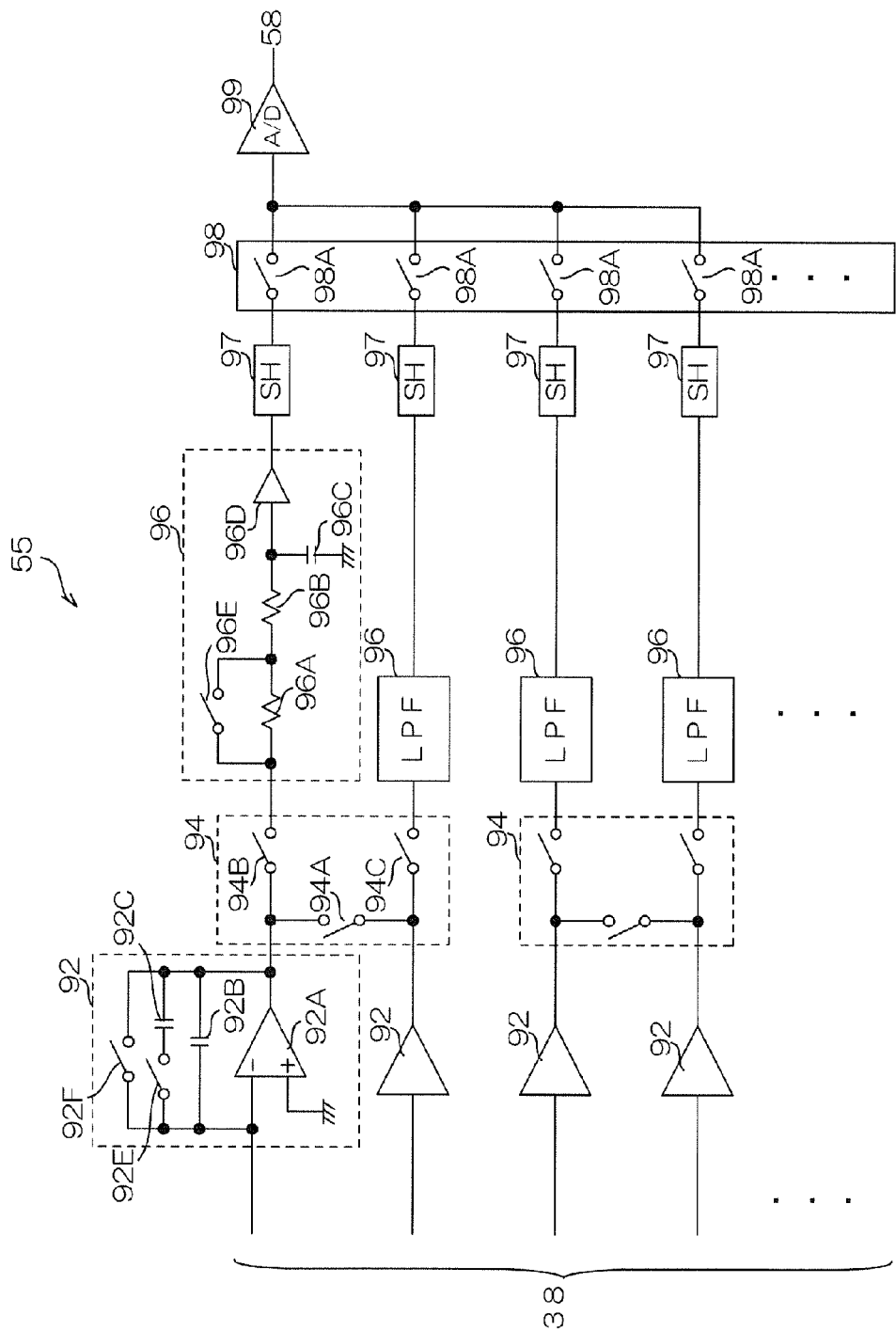
FIG. 10 is a circuit diagram showing structures of a second signal processing section in accordance with the exemplary embodiment.

Now, the structure of the second signal processing section 55 relating to the present exemplary embodiment is described. FIG. 10 shows a circuit diagram illustrating structures of the second signal processing section 55 in accordance with the present exemplary embodiment.

As shown in FIG. 10, for each of the direct connection readout wires 38, the second signal processing section 55 according to the present exemplary embodiment is equipped with a variable gain preamplifier (charge amplifier) 92, a binning section 94, a low pass filter (LPF) 96 whose low-pass frequency may be switched, and a sample and hold circuit 97 whose sample timing may be set. The second signal processing section 55 is also equipped with one each of a multiplexer 98 and an A/D converter 99.

The variable gain preamplifier 92 includes an operational amplifier 92A, whose non-inverting input side is connected to ground, and a capacitor 92B, a switch 92E, a capacitor 92C and a reset switch 92F, which are connected between the inverting input side and the output side of the operational amplifier 92A. The capacitor 92B, the switch 92E and capacitor 92C, and the reset switch 92F are connected in parallel with one another. The switch 92E and the reset switch 92F can be switched by the cassette control section 58.

The binning section 94 includes a switch 94A, which is connected between neighboring communication lines, and switches 94B and 94C, which are connected along the communication lines. The switches 94A, 94B and 94C can be switched by the cassette control section 58. In the present exemplary embodiment, a binning connection state is set by the switch 94A and switch 94B being turned on and the switch 94C being turned off, and a usual connection state is set by the switch 94B and switch 94C being turned on and the switch 94A being turned off.

The LPF 96 includes a resistor 96A, a resistor 96B, a capacitor 96C, and a switch 96E that short-circuits the resistor 96A. The switch 96E can be switched by the cassette control section 58. The sample timing of the sample and hold circuit 97 and an output selected by switches 98A, which are provided in the multiplexer 98, can also be switched by the cassette control section 58.

Each of the direct connection readout wires 38 is connected to a respective input terminal of the multiplexer 98 via the variable gain preamplifier 92, the binning section 94, the LPF 96 and the sample and hold circuit 97, in this order. An output terminal of the multiplexer 98 is connected to an input terminal of the A/D converter 99, an output terminal of which is connected to the cassette control section 58.

When the radiation amount acquisition function is operated, the cassette control section 58 first discharges (resets) charges that have accumulated at the capacitor 92B and capacitor 92C of each variable gain preamplifier 92, by turning on the switch 92E and the reset switch 92F.

Then, the cassette control section 58 sets the amplification ratio of the variable gain preamplifier 92 by setting the reset switch 92F of the variable gain preamplifier 92 to off and setting the switch 92E to on or off. The cassette control section 58 also sets the binning connection state or the usual connection state by setting the switches 94A to 94C of the binning section 94 to on or off, and sets the low-pass frequency of the LPF 96 by setting the switch 96E of the LPF 96 to on or off.

Charges that are accumulated at the capacitor 9 of each of the radiation detection pixels 32A due to the radiation X being irradiated are propagated through the direct connection readout wires 38 connected thereto in the form of electronic signals. The electronic signals propagated through the direct connection readout wires 38 are each amplified by the variable gain preamplifier 92 with the amplification ratio set by the cassette control section 58, and then combined as required by the binning section 94 and subjected to filtering processing by the LPF 96 at the low-pass frequency set by the cassette control section 58.

After the above-described setting of the amplification ratio, the binning section 94 and the low-pass frequency, the cassette control section 58 retains signal levels of the electronic signals that have been subjected to the filtering processing at the sample and hold circuit 97, by driving the sample and hold circuit 97 with a predetermined period.

The signal levels retained at the sample and hold circuits 97 are sequentially selected by the multiplexer 98 in accordance with control by the cassette control section 58, and are A/D converted by the A/D converter 99. Then, the digital data that is obtained is outputted to the cassette control section 58. The digital data outputted from the A/D converter 99 represents radiation amounts irradiated onto the radiation detection pixels 32A in the predetermined period, and corresponds to the aforementioned radiation amount information.

At the cassette control section 58, the radiation amount information that is inputted from the A/D converter 99 is sequentially stored in a pre-specified region of the RAM of the memory 58B.

As shown in FIG. 9, the console 110 is structured as a server computer. The console 110 is equipped with a display 111, which displays control menus, captured radiation images and the like, and a control panel 112, which is structured to include plural buttons and at which various kinds of information and control instructions can be inputted.

The console 110 according to the present exemplary embodiment is equipped with: a CPU 113 that administers operations of the device as a whole; a ROM 114 at which various programs, including a control program, and suchlike are stored in advance; a RAM 115 that temporarily stores various kinds of data; the HDD 116, which stores and retains various kinds of data; a display driver 117 that controls displays of various kinds of information at the display 111; and a control input detection section 118 that detects control states of the control panel 112. The console 110 is further equipped with a wireless communications section 119 that, by wireless communications, exchanges various kinds of information such as the aforementioned exposure conditions and the like with the radiation generation device 120 and exchanges various kinds of information such as image data and the like with the electronic cassette 40.

The CPU 113, ROM 114, RAM 115, HDD 116, display driver 117, control input detection section 118 and wireless communications section 119 are connected to one another by a system bus. Thus, the CPU 113 may access the ROM 114, RAM 115 and HDD 116, control displays of various kinds of information at the display 111 via the display driver 117 and, via the wireless communications section 119, control transmission and reception of various kinds of information to and from the radiation generation device 120 and the electronic cassette 40. The CPU 113 may also acquire states of control by users from the control panel 112 via the control input detection section 118.

The radiation generation device 120 is provided with the radiation source 121, a wireless communications section 123, and a radiation source control section 122. The wireless communications section 123 exchanges various kinds of information such as the exposure conditions and the like with the console 110. The control section 122 controls the radiation source 121 on the basis of received exposure conditions.

The radiation source control section 122 includes a microcomputer, and stores the received exposure conditions and the like. The exposure conditions received from the console 110 include information such as a tube voltage, a tube current and the like. The radiation source control section 122 causes the radiation X to be irradiated from the radiation source 121 in accordance with the received exposure conditions.

Next, operation of the imaging system 104 relating to the present exemplary embodiment is described.

Figure 11:
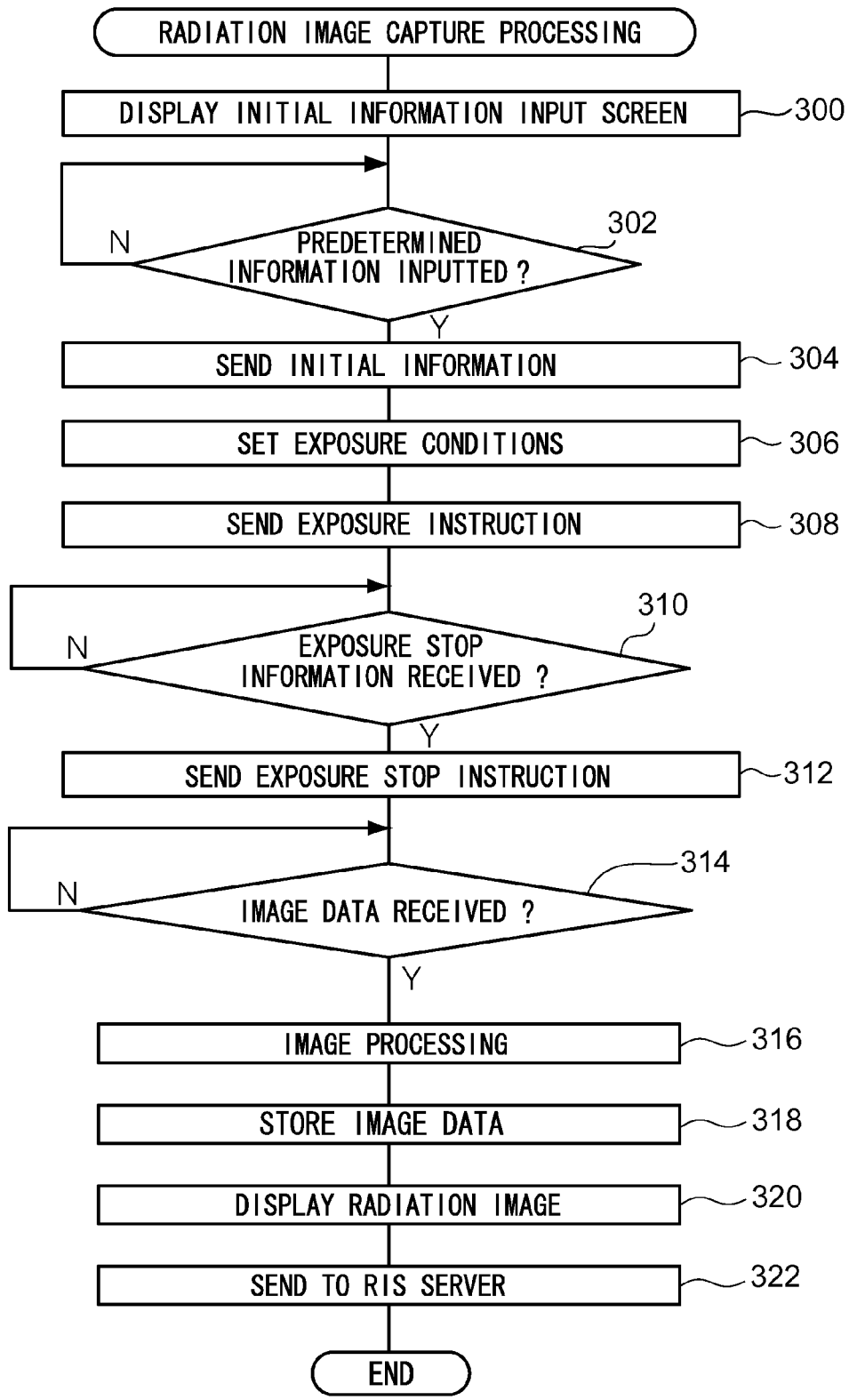
FIG. 11 is a flowchart showing the flow of processing of a radiation image capture processing control program in accordance with the exemplary embodiment.

First, operation of the console 110 when capturing a radiation image is described with reference to FIG. 11. FIG. 11 is a flowchart showing the flow of processing of a radiation image capture processing program that is executed by the CPU 113 of the console 110 when an instruction to execute the same is inputted via the control panel 112. This program is memorized beforehand in a predetermined region of the ROM 114.

In step 300 of FIG. 11, the display driver 117 is controlled such that a pre-specified initial information input screen is displayed by the display 111. Then, in step 302, the CPU 113 waits for the input of predetermined information.

FIG. 12 shows an example of the initial information input screen that is displayed at the display 111 by the processing of step 300. As shown in FIG. 12, the initial information input screen according to the present exemplary embodiment displays a message prompting the input of the name of the subject of whom a radiation image will be captured, the imaging target portion, the subject's posture at the time of imaging, and exposure conditions of the radiation X during the imaging (in the present exemplary embodiment, a tube voltage and tube current when the radiation X is exposed), along with input fields for these items of information.

When the initial information input screen shown in FIG. 12 is displayed at the display 111, the operator inputs at the respectively corresponding input fields, via the control panel 112, the name of the subject who is the object of imaging, the imaging target portion, the posture at the time of imaging, and the exposure conditions.

Then, in a case in which the posture during imaging is standing or reclining, the operator retains the electronic cassette 40 at the retention portion 162 of the standing table 160 or the retention portion 166 of the reclining table 164, positions the radiation source 121 at a position that corresponds with the electronic cassette 40, and then arranges the imaging subject at the predetermined imaging position. In a case of capturing a radiation image in a state in which the electronic cassette 40 is not retained at a retention portion, such as when the imaging target portion is an arm area or a leg area, the operator positions the imaging subject, the electronic cassette 40 and the radiation source 121 into a state in which the imaging target portion can be imaged. Then, via the control panel 112, the operator operates a "Complete" button displayed near the bottom end of the initial information input screen. When the Complete button is clicked by the operator, the result of the determination in step 302 is affirmative and the CPU 113 proceeds to step 304.

In step 304, the information inputted into the initial information input screen (hereinafter referred to as initial information) is sent to the electronic cassette 40 via the wireless communications section 119. Then, in step 306, the exposure conditions included in the initial information are set by transmission of the exposure conditions to the radiation generation device 120 via the wireless communications section 119. Accordingly, the radiation source control section 122 of the radiation generation device 120 prepares for exposure with the received exposure conditions.

In step 308, instruction information instructing the start of exposure is sent to the radiation generation device 120 and the electronic cassette 40 via the wireless communications section 119.

In response, the radiation source 121 starts emission of the radiation X with a tube voltage and tube current according to the exposure conditions that the radiation generation device 120 received from the console 110. The radiation X emitted from the radiation source 121 reaches the electronic cassette 40 after passing through the imaging subject.

Meanwhile, when the cassette control section 58 of the electronic cassette 40 receives the instruction information instructing the start of exposure, the cassette control section 58 acquires the radiation amount information with the aforementioned radiation amount acquisition function, and waits until a radiation amount represented by the acquired radiation amount information is at or above a pre-specified first threshold value, which is a value for detecting that an irradiation of radiation has started. Then, the electronic cassette 40 starts operations for capturing the radiation image. Subsequently, at a time at which a cumulative value of radiation amounts represented by the radiation amount information reaches a pre-specified second threshold value, which is a value for stopping the exposure of the radiation X, the electronic cassette 40 stops the imaging operation and sends exposure stop information to the console 110. The second threshold value is based on the imaging target portion, exposure conditions and the like included in the initial information.

Accordingly, in step 310, the CPU 113 waits for reception of the exposure stop information. Then, in step 312, instruction information instructing that the exposure of the radiation X be stopped is sent to the radiation generation device 120 via the wireless communications section 119. In response, the exposure of the radiation X from the radiation source 121 is stopped.

Meanwhile, when the electronic cassette 40 stops the operation for capturing the radiation image, the electronic cassette 40 sends the image data obtained by the imaging to the console 110.

Accordingly, in step 314, the CPU 113 waits until the image data is received from the electronic cassette 40. In step 316, image processing is executed to apply the aforementioned missing pixel correction processing to the received image data, and then apply various kinds of correction such as shading correction and the like.

In step 318, the image data to which the image processing has been applied (hereinafter referred to as corrected image data) is stored in the HDD 116. Then, in step 320, the CPU 113 controls the display driver 117 such that a radiation image represented by the corrected image data is displayed by the display 111, for checking or the like.

In step 322, the corrected image data is sent to the RIS server 150 via the hospital internal network 102, after which the present radiation image capture processing program ends. The corrected image data sent to the RIS server 150 is stored in the database 150A, and doctors may view the captured radiation image and conduct diagnostics and the like.

Figure 13:
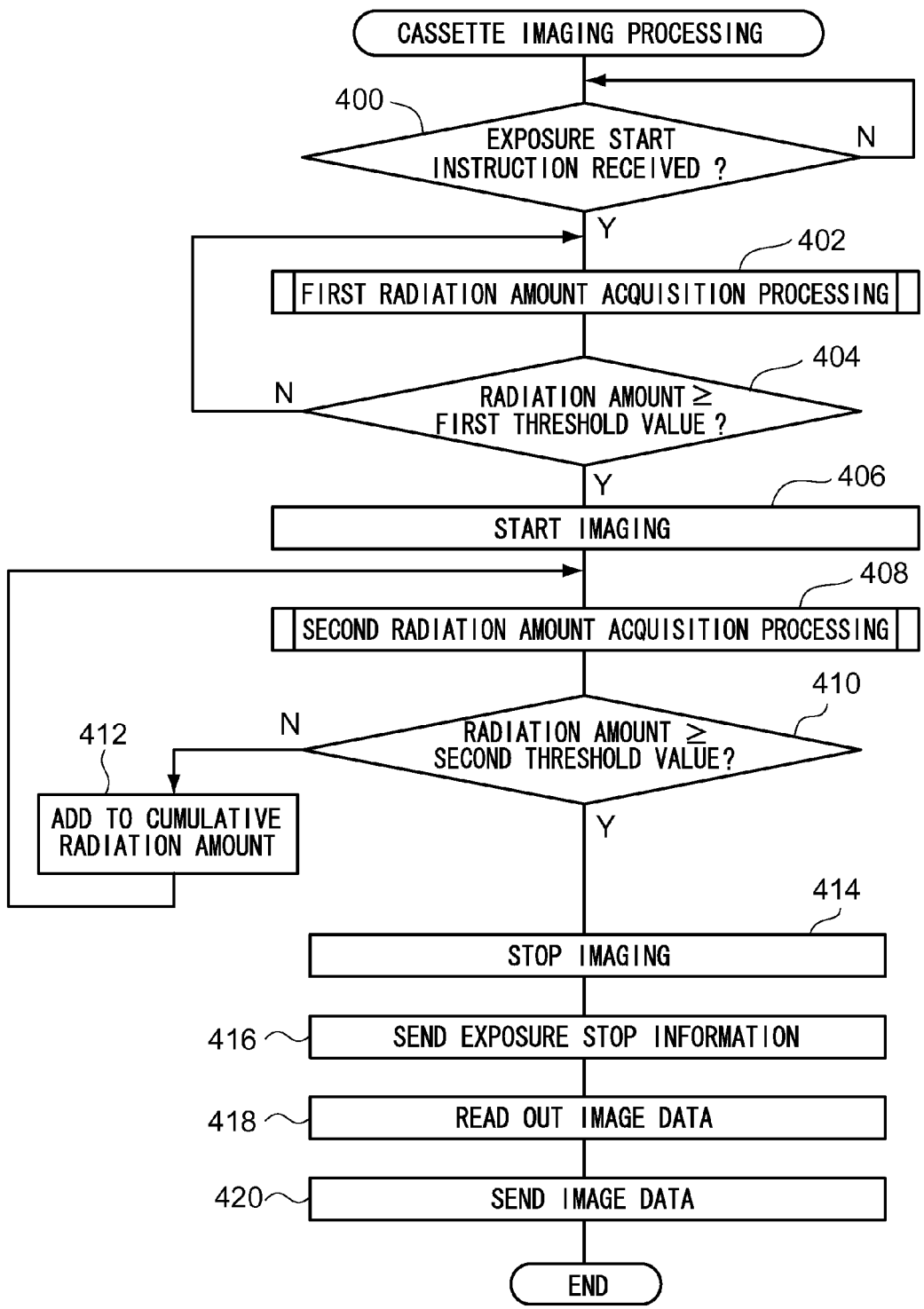
FIG. 13 is a flowchart showing the flow of processing of a cassette imaging processing control program in accordance with the exemplary embodiment.

Next, operation of the electronic cassette 40 when the above-described initial information is received from the console 110 is described with reference to FIG. 13. FIG. 13 is a flowchart showing the flow of processing of a cassette imaging processing program that is executed by the CPU 58A of the cassette control section 58 of the electronic cassette 40 at this time. This program is memorized in advance in a predetermined region of the memory 58B.

In step 400 of FIG. 13, the CPU 58A waits for reception from the console 110 of the above-mentioned instruction information instructing the start of exposure. Then, in step 402, the CPU 58A executes a first radiation amount acquisition processing routine program, which acquires radiation amount information with the aforementioned radiation amount acquisition function.

Figure 14:
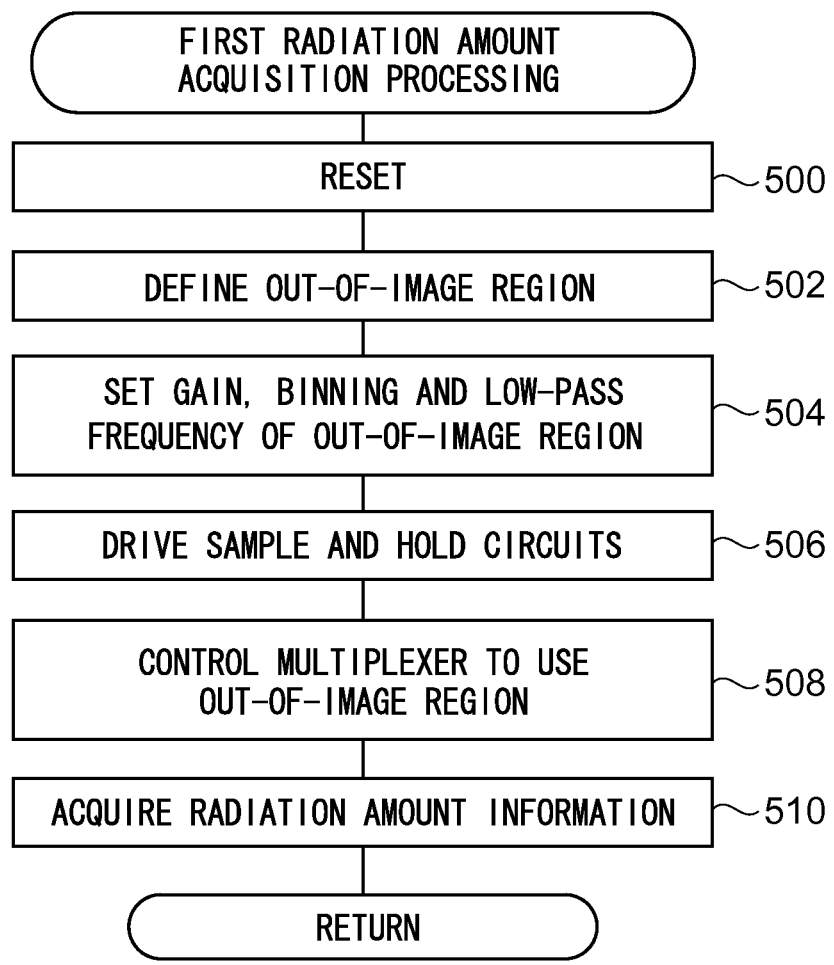
FIG. 14 is a flowchart showing the flow of processing of a first radiation amount acquisition processing routine program in accordance with the exemplary embodiment.

Herebelow, the first radiation amount acquisition processing routine program according to the present exemplary embodiment is described with reference to FIG. 14. FIG. 14 is a flowchart showing the flow of processing of the first radiation amount acquisition processing routine program according to the present exemplary embodiment. This program is memorized in advance in a predetermined region of the memory 58B.

In step 500 of FIG. 14, the CPU 58A discharges charges that have accumulated at the capacitor 92B and capacitor 92C of every variable gain preamplifier 92 by turning on the switch 92E and the reset switch 92F. The CPU 58A also resets the second signal processing section 55 by discharging a retained signal level from every sample and hold circuit 97.

In step 502, the CPU 58A defines an out-of-image region, which is a region of the imaging region of the radiation detector 20 at which the imaging target portion is not disposed. In the electronic cassette 40 according to the present exemplary embodiment, for each of the imaging target portions that are anticipated, information representing the positions of an out-of-image region/regions is stored in advance in a predetermined region of the ROM of the memory 58B. The CPU 58A defines the out-of-image region by reading, from this information, information representing the positions of an out-of-image region/regions that correspond to the imaging target portion included in the initial information.

In step 504, the CPU 58A specifies the radiation detection pixels 32A that are disposed in the out-of-image region defined by the processing of step 502, and sets the amplification ratio of each variable gain preamplifier 92 corresponding to the specified radiation detection pixels 32A (hereinafter referred to as "out-of-image region pixels") to the lower amplification ratio. The CPU 58A also sets the connection state of each binning section 94 of these pixels to the usual connection state and sets the low-pass frequency of each LPF 96 of these pixels to the higher frequency.

In step 506, the CPU 58A drives every sample and hold circuit 97 corresponding to the out-of-image region pixels for a predetermined period and thus retains the signal levels of electronic signals that have been subjected to filtering processing at the sample and hold circuits 97. Then, in step 508, the CPU 58A controls the multiplexer 98 such that the output signals from the sample and hold circuits 97 corresponding to the out-of-image region pixels are sequentially selected and outputted.

By the processing described above, digital data representing the signal levels of electronic signals that have been amplified by the variable gain preamplifiers 92 and subjected to filtering by the LPFs 96 is sequentially outputted from the A/D converter 99 to serve as radiation amount information. Accordingly, in step 510 the CPU 58A sequentially acquires the radiation amount information outputted from the A/D converter 99, after which the first radiation amount acquisition processing routine program ends. When the first radiation amount acquisition processing routine program ends, the CPU 58A proceeds to step 404 of the cassette imaging processing program shown in FIG. 13 (the main routine).

In step 404, the CPU 58A makes a determination as to whether a radiation amount represented by the information acquired by the above processing of step 402 (in the present exemplary embodiment, an average value of radiation amounts represented by the radiation amount information sequentially outputted from the A/D converter 99) is at least the aforementioned first threshold. If the result of the determination is negative, the CPU 58A returns to step 402. On the other hand, if the result of the determination is affirmative, it is determined that the exposure of the radiation X from the radiation source 121 has started and the CPU 58A advances to step 406.

In step 406, the CPU 58A discharges charges that have accumulated at the capacitor 9 of each of the pixels 32 of the radiation detector 20, and then, by restarting the accumulation of charges at each capacitor 9, starts the radiation image imaging operation. Then, in step 408, the CPU 58A executes a second radiation amount acquisition processing routine program, which acquires radiation amounts with the aforementioned radiation amount acquisition function.

Figure 15:
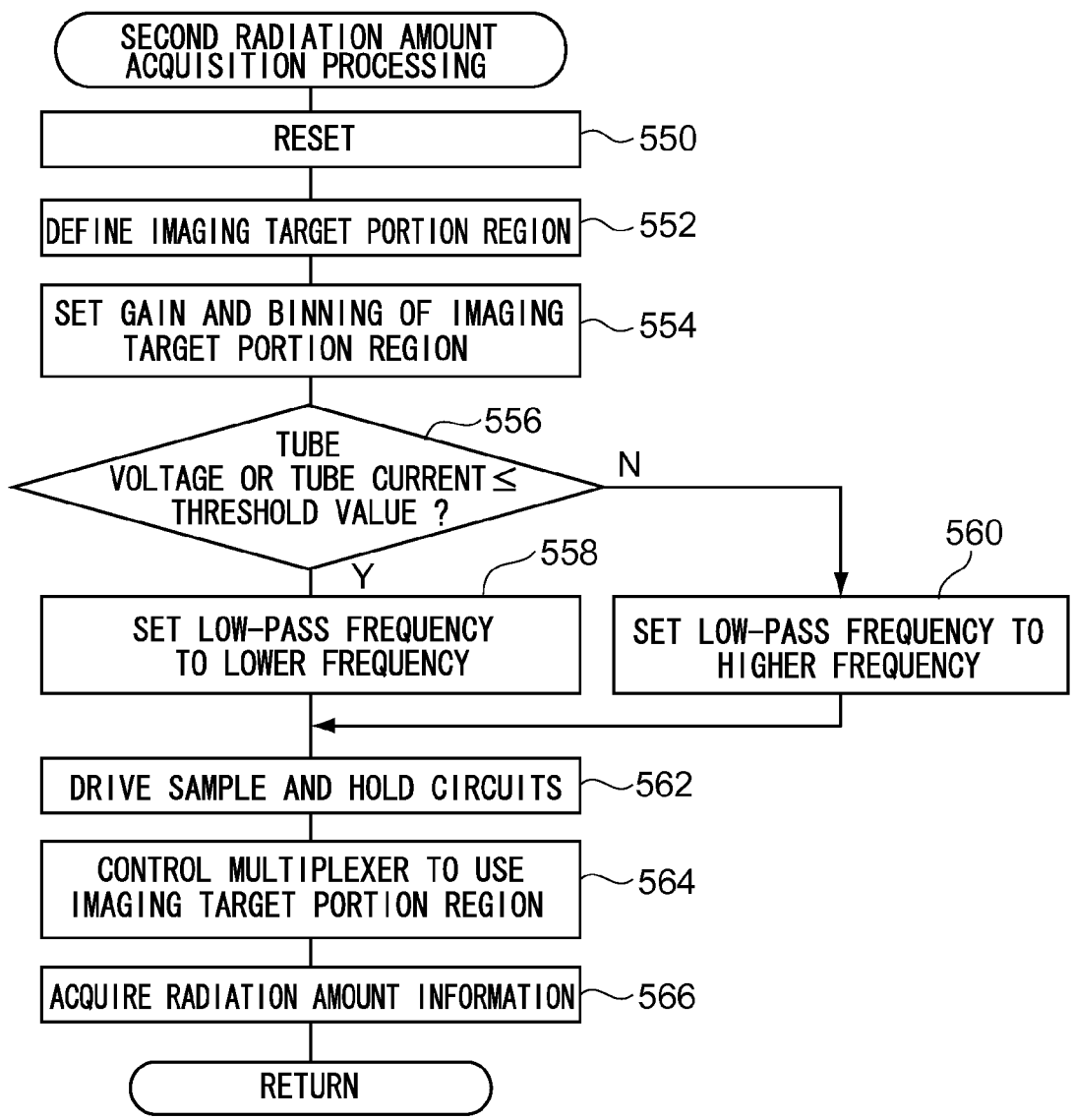
FIG. 15 is a flowchart showing the flow of processing of a second radiation amount acquisition processing routine program in accordance with the exemplary embodiment.

Herebelow, the second radiation amount acquisition processing routine program according to the present exemplary embodiment is described with reference to FIG. 15. FIG. 15 is a flowchart showing the flow of processing of the second radiation amount acquisition processing routine program in accordance with the present exemplary embodiment. This program is memorized in advance in a predetermined region of the memory 58B.

In step 550 of FIG. 15, the CPU 58A discharges charges that have accumulated at the capacitor 92B and capacitor 92C of every variable gain preamplifier 92 by turning on the switch 92E and the reset switch 92F. The CPU 58A also resets the second signal processing section 55 by discharging a retained signal level from every sample and hold circuit 97.

In step 552, the CPU 58A defines an imaging target portion region, which is a region of the imaging region of the radiation detector 20 at which the imaging target portion is disposed. In the electronic cassette 40 according to the present exemplary embodiment, for each of the anticipated imaging target portions, information representing the positions of an imaging target portion region is stored in advance in a predetermined region of the ROM of the memory 58B. The CPU 58A defines the imaging target portion region by reading, from this information, information representing the positions of an imaging target portion region that corresponds to the imaging target portion included in the initial information.

In step 554, the CPU 58A specifies the radiation detection pixels 32A that are disposed in the imaging target portion region defined by the processing of step 552, and sets the amplification ratio of each variable gain preamplifier 92 corresponding to the specified radiation detection pixels 32A (hereinafter referred to as "imaging target portion region pixels") to the higher amplification ratio. The CPU 58A also sets the connection state of each binning section 94 of these pixels to the binning connection state.

In step 556, the CPU 58A makes a determination as to whether at least one of the tube voltage and tube current in the exposure conditions included in the initial information is below a corresponding threshold specified in advance for each. If the result of the determination is affirmative, the CPU 58A advances to step 558, sets the low-pass frequency of each LPF 96 of the imaging target portion region pixels to the lower frequency, and then advances to step 562. On the other hand, if the result of the determination in step 556 is negative, the CPU 58A advances to step 560, sets the low-pass frequency of each LPF 96 of the imaging target portion region pixels to the higher frequency, and then advances to step 562.

In step 562, the CPU 58A drives every sample and hold circuit 97 corresponding to the imaging target portion region pixels for a predetermined period and thus retains the signal levels of the electronic signals that have been subjected to filtering processing at the sample and hold circuits 97. Then, in step 564, the CPU 58A controls the multiplexer 98 such that the output signals from the sample and hold circuits 97 corresponding to the imaging target portion region pixels are sequentially selected and outputted.

By the processing described above, digital data representing the signal levels of electronic signals that have been amplified by the variable gain preamplifiers 92 and then combined by the binning portions 94 and subjected to filtering by the LPFs 96 is sequentially outputted from the A/D converter 99 to serve as radiation amount information. Accordingly, in step 566 the CPU 58A sequentially acquires the radiation amount information outputted from the A/D converter 99, after which the second radiation amount acquisition processing routine program ends. When the second radiation amount acquisition processing routine program ends, the CPU 58A proceeds to step 410 of the cassette imaging processing program shown in FIG. 13 (the main routine).

In step 410, the CPU 58A makes a determination as to whether a radiation amount represented by the information acquired by the above processing of step 408 (in the present exemplary embodiment, an average value of radiation amounts represented by the radiation amount information sequentially outputted from the A/D converter 99) is at least the aforementioned second threshold. If the result of the determination is negative, the CPU 58A advances to step 412, adds the radiation amount acquired by the above-described processing of step 408 to a cumulative total, and returns to step 408. On the other hand, if the result of the determination is affirmative, the CPU 58A advances to step 414. While the above-described processing of steps 408 to 412 is being repeatedly executed, the CPU 58A makes determinations in step 410 as to whether the cumulative radiation amount is at least the second threshold.

In step 414, the CPU 58A stops the imaging operation that was started by the above-described processing of step 406. Then, in step 416, the CPU 58A sends the aforementioned exposure stop information to the console 110 via the wireless communications section 60.

In step 418, the CPU 58A controls the gate line driver 52, On signals are sequentially outputted to the gate lines 34 one line at a time from the gate line driver 52, and the thin film transistors 10 connected to the respective gate lines 34 are sequentially turned on line by line.

When the radiation detector 20 turns on the thin film transistors 10 connected to the gate lines 34 line by line, the charges accumulated in the capacitors 9 flow out into the respective data lines 36 in the form of electronic signals, line by line. The electronic signals flowing into the data lines 36 are converted to digital image data by the first signal processing section 54 and stored in the image memory 56.

The CPU 58A reads out the image data stored in the image memory 56 by step 418 and then, in step 420, sends the read image data to the console 110 via the wireless communications section 60, after which the present cassette imaging processing program ends.

Now, as shown in FIG. 8, in the electronic cassette 40 according to the present exemplary embodiment, the radiation detector 20 is incorporated such that the radiation X is irradiated thereon from the side thereof at which the TFT substrate 30 is disposed.

Figure 16:
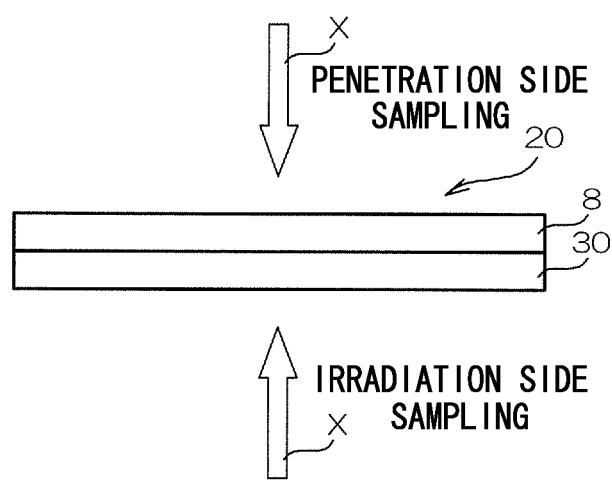
FIG. 16 is a sectional side diagram for explaining penetration side sampling and irradiation side sampling of radiation images.

In a case in which, as shown in FIG. 16, the radiation is irradiated from the side of the radiation detector 20 at which the scintillator 8 is formed and the radiation detector 20 reads the radiation image with the TFT substrate 30 that is provided at a rear face side relative to the face at which the radiation is incident, which case is referred to as penetration side sampling (PSS), light is more strongly emitted from the side of the scintillator 8 that is at the upper face side in FIG. 16 (i.e., to the opposite side thereof from the side at which the TFT substrate 30 is disposed). In a case in which the radiation is irradiated from the side of the radiation detector 20 at which the TFT substrate 30 is formed and the radiation detector 20 reads the radiation image with the TFT substrate 30 that is provided at a front face side relative to the face at which the radiation is incident, which case is referred to as irradiation side sampling (ISS), radiation that has passed through the TFT substrate 30 is incident on the scintillator 8 and light is more strongly emitted from the side of the scintillator 8 at which the TFT substrate 30 is disposed. Charges are generated by the light emitted from the scintillator 8 to the sensor portions 13 provided at the TFT substrate 30. Therefore, in a case in which the radiation detector 20 is of an ISS type, light emission positions of the scintillator 8 are closer to the TFT substrate 30 than in a case in which the radiation detector 20 is of a PSS type. As a result, the resolution of the radiation images obtained by imaging is higher.

In the radiation detector 20, the photoelectric conversion film 4 is constituted of an organic photoelectric conversion material, and hardly any radiation is absorbed by the photoelectric conversion film 4. Therefore, because amounts of radiation absorbed by the photoelectric conversion film 4 are small even if the radiation is passing through the TFT substrate 30 in accordance with ISS, the radiation detector 20 according to the present exemplary embodiment may suppress a reduction in sensitivity to the radiation. In ISS, the radiation passes through the TFT substrate 30 and reaches the scintillator 8. Thus, in a case in which the photoelectric conversion film 4 of the TFT substrate 30 is constituted by an organic photoelectric conversion material, hardly any radiation is absorbed by the photoelectric conversion film 4 and attenuation of the radiation may be kept low. Therefore, ISS is favorable.

A non-crystalline oxide that constitutes the active layer 17 of each thin film transistor 10, the organic photoelectric conversion material that constitutes the photoelectric conversion film 4, and suchlike are all capable of film formation at low temperatures. Therefore, the substrate 1 may be formed of a plastic resin, aramid or bionanofiber that absorbs small amounts of the radiation. Because radiation absorption amounts of the substrate 1 that is formed thus are small, even in a case in which the radiation passes through the TFT substrate 30 in accordance with ISS, a reduction in sensitivity to the radiation may be suppressed.

According to the present exemplary embodiment, the radiation detector 20 is adhered to the top plate 41B inside the casing 41 such that the TFT substrate 30 is at the top plate 41B side of the radiation detector 20, as illustrated in FIG. 8. If the insulating substrate 1 is formed of a plastic resin, aramid or bionanofiber with high stiffness, then because the radiation detector 20 itself is stiff, the top plate 41B of the casing 41 may be formed to be thin. Moreover, in a case in which the insulating substrate 1 is formed of a plastic resin, aramid or bionanofiber with high stiffness, because the radiation detector 20 itself has flexibility, the radiation detector 20 is resistant to breakage even if an impact is applied to the imaging region 41A.

As is described in detail hereabove, in the present exemplary embodiment, the radiation detection pixels (the radiation detection pixels 32A of the present exemplary embodiment) are configured with characteristics that are alterable, and the characteristics are set in accordance with the imaging conditions of a radiation image. Therefore, radiation irradiation states may be detected more accurately than in a case in which this setting is not performed.

In the present exemplary embodiment, a characteristic may be set by switching between positions of the radiation detection pixels in accordance with the imaging conditions. Thus, radiation irradiation states may be detected accurately even in, for example, a case in which the imaging target portion is disposed at only a portion of the imaging region, or the like.

In the present exemplary embodiment, amplifiers (in the present exemplary embodiment, the variable gain preamplifiers 92) that amplify signals represented by charges accumulated by the radiation detection pixels by a pre-specified amplification ratio are provided, and a characteristic may be set by setting the amplification ratio in accordance with the imaging conditions. In addition, low-pass filters (in the present exemplary embodiment, the LPFs 96) that apply low-pass processing with a pre-specified low-pass frequency to the signals represented by the charges accumulated by the radiation detection pixels are provided, and a characteristic may be set by setting the low-pass frequency in accordance with the imaging conditions. Further, switching units (in the present exemplary embodiment, the binning portions 94) that switch whether or not the signals represented by the charges accumulated by the radiation detection pixels are combined in groups of a pre-specified number are provided, and a characteristic may be set by switching whether or not the signals are combined in accordance with the imaging conditions. Thus, the characteristics of the radiation detection pixels may be set with ease.

In the present exemplary embodiment, the characteristics are set in accordance with whether the start of an irradiation of radiation is to be detected on the basis of the radiation detected by the radiation detection pixels or whether radiation amounts of radiation are to be detected. Therefore, radiation irradiation states may be detected more accurately in accordance with the object of detection.

In the present exemplary embodiment, the radiation detector is equipped with dedicated wiring (in the present exemplary embodiment, the direct connection readout wires 38) for reading out the accumulated charges from the radiation detection pixels. Therefore, radiation may be detected irrespective of radiation image capture operations. As a result, radiation images may be captured more quickly.

Hereabove, the present invention has been described using an exemplary embodiment, but the technical scope of the present invention is not to be limited to the scope described in the above exemplary embodiment. Numerous modifications and improvements may be applied to the above exemplary embodiment within a scope not departing from the spirit of the invention, and modes to which these modifications and/or improvements are applied are to be encompassed by the technical scope of the invention.

Furthermore, the exemplary embodiment described above is not to limit the inventions relating to the claims, and means for achieving the invention are not necessarily to be limited to all of the combination of features described in the exemplary embodiment. Various stages of the invention are included in the above exemplary embodiment, and various inventions may be derived by suitable combinations of the plural structural elements that are disclosed. If some structural element is omitted from the totality of structural elements illustrated in the exemplary embodiment, as long as the effect thereof is provided, a configuration from which the some structural element is omitted may be derived to serve as the invention.

Figure 6:
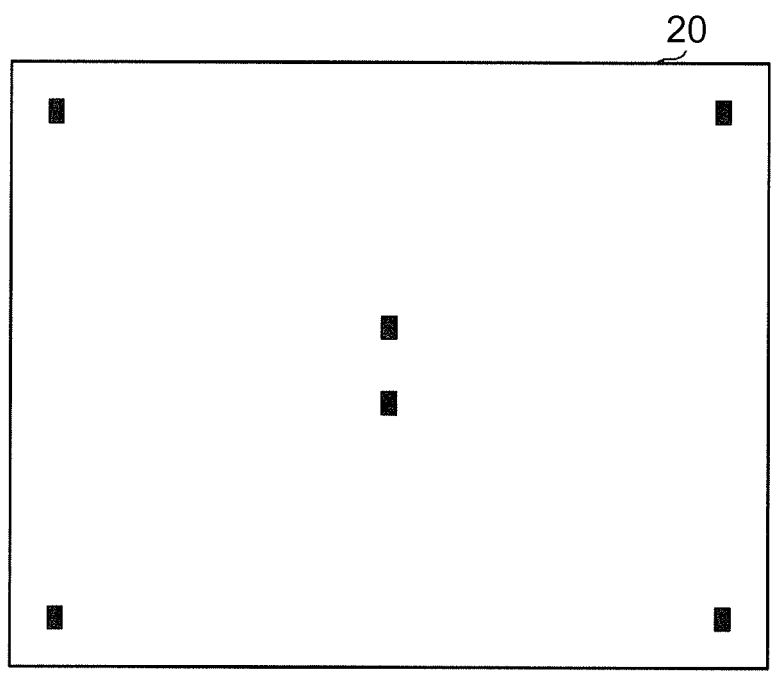
FIG. 6 is a plan diagram showing a state of arrangement of pixels for radiation detection in accordance with the exemplary embodiment.

For example, in the exemplary embodiment described above, a case is described in which the radiation detection pixels 32A are disposed at a central portion detection region and peripheral edge portion detection regions so as to be symmetrical both in an up-and-down direction and in a leftand-right direction, as shown in FIG. 6. However, the present invention is not limited thus, and the positions of arrangement of the radiation detection pixels 32A are not particularly limited. However, when the radiation detection pixels are disposed to be symmetrical in both the left-and-right direction and the up-and-down direction as in the present exemplary embodiment, the electronic cassette 40 may be used without concern about the left/right/up/down orientation. Thus, usability may be improved, which is preferable.

When the radiation detection pixels 32A are disposed so as to be symmetrical between up and down and left and right, an orientation detector such as an acceleration sensor, a gyroscope or the like may be provided in the electronic cassette 40. Hence, modes in which out-of-image region pixels and imaging target portion region pixels are defined in accordance with a determined orientation of the electronic cassette 40 are possible.

In the exemplary embodiment described above, some of the pixels 32 provided in the radiation detector 20 are used as the radiation detection pixels 32A. Therefore, it is clearly preferable to interpolate the neighboring radiation detection pixels 32A to an extent at which missing pixel correction may be implemented.

In the exemplary embodiment described above, a case is described in which some of the pixels 32 provided in the radiation detector 20 are used as the radiation detection pixels 32A, but the present invention is not limited thus. For example, a mode is possible in which the radiation detection pixels 32A are layered in the radiation detector 20 as a separate layer from the pixels 32. In this case, because no missing pixels occur, the quality of a radiation image may be improved compared to the exemplary embodiment described above.

In the exemplary embodiment described above, a case is described in which the radiation detection pixels 32A are dedicated pixels that detect radiation. However, the present invention is not limited thus, and a mode is possible in which the radiation detection pixels 32A and the radiation image acquisition pixels 32B are combined.

In the exemplary embodiment described above, a case is described in which all of the amplification ratio of the variable gain preamplifiers 92, the binning state of the binning sections 94 and the low-pass frequency of the LPFs 96 can be switched in accordance with imaging conditions. However, the present invention is not limited thus and modes are possible in which one or a combination of two of these can be switched.

In the exemplary embodiment described above, a case is described in which the amplification ratio of each variable gain preamplifier 92 and the low-pass frequency of each LPF 96 can be switched between two levels. However, the present invention is not limited thus and modes are possible in which these can be switched between three or more levels. Moreover, the number of electronic signals combined by each binning section 94 is not limited to two and modes are possible in which the number is three or more.

In the exemplary embodiment described above, a case is described in which the radiation detection pixels 32A are used for detecting the start of an irradiation of radiation and radiation amounts. However, the present invention is not limited thus and a mode is possible in which the radiation detection pixels 32A are used for detecting the stop of an irradiation of radiation.

If the radiation detection pixels 32A are used for detecting a radiation irradiation start and radiation irradiation stop, a mode is possible in which respectively different radiation detection pixels 32A are used to detect an irradiation start and an irradiation end, and the amplification ratio of each variable gain preamplifier 92 corresponding to the radiation detection pixels 32A used for detecting the radiation start is set higher than the amplification ratio of each variable gain preamplifier 92 corresponding to the radiation detection pixels 32A used for detecting the radiation end. Thus, the start of an irradiation of radiation may be detected in a shorter duration.

Furthermore, the respective setting conditions described in the above exemplary embodiment—the amplification ratio of the variable gain preamplifiers, binning state of the binning portions, and low-pass frequency of the LPFs—are examples and exemplary modes as illustrated herebelow may be employed.

In regard to the amplification ratio of the variable gain preamplifiers, modes such as the following may be illustrated: a mode in which the amplification ratio is set lower when the irradiation amount of the radiation X is higher; a mode in which a higher amplification ratio is set when video imaging is performed than when still images are captured; and a mode in which a relatively high amplification ratio is set when a radiation irradiation start is to be detected and a relatively low amplification ratio is set when a radiation irradiation end or an irradiation amount is to be detected.

In regard to binning states of the binning portions, modes such as the following may be illustrated: a mode in which the binning number is smaller when the irradiation amount of the radiation X is higher; a mode in which a larger binning number is set when video imaging is performed than when still images are captured; and a mode in which a relatively large binning number is set when a radiation irradiation start is to be detected and a relatively small binning number is set when a radiation irradiation end or an irradiation amount is to be detected.

In regard to the low-pass frequency of the LPFs, modes such as the following may be illustrated: a mode in which the low-pass frequency is set lower when the tube current and/or tube voltage is lower when the radiation X is being irradiated; and a mode in which a relatively low low-pass frequency is set as a low-pass frequency corresponding to radiation detection pixels that are disposed in the imaging region at which the imaging target portion is disposed.

In the exemplary embodiment described above, a case is described in which the radiation detection pixels 32A that are arranged in the row direction of the radiation detector 20 are connected to the common direct connection readout wires 38. However, the present invention is not limited thus, and a mode is possible in which all of the radiation detection pixels 32A are individually connected to different direct connection readout wires 38.

In the exemplary embodiment described above, a case is described in which the image data obtained by imaging of a radiation image is recorded to the database 150A. However, the present invention is not limited thus. Modes are possible in which one or both of the initial information and the setting conditions of the second signal processing section 55 used when obtaining the data is recorded in association with the image data.

In the exemplary embodiment described above, a case is described in which each sensor portion 13 is constituted with an organic photoelectric conversion material that generates charges when the light generated by the scintillator 8 is received. However, the present invention is not limited thus, and modes are possible in which a constitution that does not include an organic photoelectric conversion material is employed as the sensor portion 13.

In the exemplary embodiment described above, a case is described in which the case 42 that accommodates the cassette control section 58, the power supply section 70 and the like is disposed inside the casing 41 of the electronic cassette 40 so as not to overlap with the radiation detector 20, but this is not limiting. For example, the radiation detector 20 may be disposed so as to overlap with the cassette control section 58 and power supply section 70 or the like.

In the exemplary embodiment described above, a case is described in which communications between the electronic cassette 40 and the console 110 and between the radiation generation device 120 and the console 110 are performed by wireless. However, the present invention is not limited thus. For example, modes are possible in which communications over at least one of these links are performed by wire.

In the exemplary embodiment described above, a case is described in which X-rays are employed as the radiation. However, the present invention is not limited thus and modes are possible in which other radiation such as gamma rays or the like is employed.

Further, the structure of the RIS 100 described in the above exemplary embodiment (see FIG. 1), the structure of the radiography imaging room (see FIG. 2), the structure of the electronic cassette 40 (see FIG. 3 to FIG. 8 and FIG. 10) and the structure of the imaging system 104 (see FIG. 9) are examples. It will be clear that unnecessary portions may be removed, new portions may be added, and states of connection and the like may be modified, within a scope not departing from the spirit of the present invention.

The structure of the initial information described in the above exemplary embodiment is also an example, and it will be clear that unnecessary information may be removed and new information may be added within a scope not departing from the spirit of the present invention.

The flows of processing of the various programs described in the above exemplary embodiment (see FIG. 11 and FIG. 13 to FIG. 15) are also examples, and it will be clear that unnecessary steps may be removed, new steps may be added and sequences of processing may be rearranged, within a scope not departing from the spirit of the present invention.

The structure of the initial information input screen described in the above exemplary embodiment (see FIG. 12) is also an example, and it will be clear that unnecessary information may be removed and new information may be added within a scope not departing from the spirit of the present invention.

According to the radiographic imaging device in accordance with the first aspect, at the radiation detector, the plural pixels for radiation image acquisition that are arranged in an array pattern in the radiation image imaging region acquire image information that expresses a radiation image by respectively converting irradiated radiation to electric charges and accumulating the electric charges. Meanwhile, the plural pixels for radiation detection that are disposed in the imaging region and whose characteristics may be altered detect irradiated radiation by respectively converting the irradiated radiation to electric charges and accumulating the electric charges.

In the present invention, imaging conditions for a radiation image are acquired by the acquisition unit, and the characteristics are set by the setting unit in accordance with the imaging conditions required by the acquisition unit.

Thus, according to the radiographic imaging device in accordance with the first aspect, the radiation detection pixels are configured with characteristics thereof being alterable, and the characteristics are set in accordance with imaging conditions of a radiation image. Thus, radiation irradiation states may be detected more accurately than in a case in which this setting is not performed.

As a second aspect of the present invention, the setting unit may set the characteristic by switching between positions of the radiation detection pixels in accordance with the imaging condition. Thus, if, for example, an imaging target portion is disposed at only a portion of the imaging region or suchlike, radiation irradiation conditions may be accurately detected.

A third aspect of the present invention may further include amplifiers that amplify signals represented by the charges accumulated by the radiation detection pixels by a pre-specified amplification ratio, wherein the setting unit sets the characteristic by setting the amplification ratio in accordance with the imaging condition. A fifth aspect may further include low-pass filters that apply low-pass filtering with a pre-specified low-pass frequency to signals represented by the charges accumulated by the radiation detection pixels, wherein the setting unit sets the characteristic by setting the low-pass frequency in accordance with the imaging condition. A sixth aspect may further include a switching unit that switches whether or not signals represented by the charges accumulated by the radiation detection pixels are combined in groups of a pre-specified number, wherein the setting unit sets the characteristic by switching whether or not the signals are combined in accordance with the imaging condition. Thus, the characteristics of the pixels for radiation detection may be set with ease.

In particular, in the third aspect, a fourth aspect of the present invention may further include a detection unit that detects the start of an irradiation of radiation and the end of an irradiation of radiation using mutually different the radiation detection pixels, wherein the setting unit sets the amplification ratio of the amplifiers that correspond with the radiation detection pixels that are used for detecting the radiation irradiation start to be higher than the amplification ratio of the amplifiers that correspond with the radiation detection pixels that are used for detecting the radiation irradiation end. Thus, the start of an irradiation of radiation may be detected in a shorter duration.

As a seventh aspect of the present invention, the setting unit may set the characteristic in accordance with whether a radiation irradiation start or radiation irradiation end is to be detected or an irradiation amount of the radiation is to be detected on the basis of radiation detected by the radiation detection pixels. Thus, radiation irradiation states may be detected more accurately in accordance with objects of detection.

As an eighth aspect of the present invention, the imaging condition may include at least one of an imaging target portion, a region in which the imaging target portion is disposed during imaging of the radiation image, whether the imaging is of a video image or a still image, and an irradiation amount of radiation. Thus, radiation irradiation states may be detected more accurately in accordance with applied imaging conditions.

As a ninth aspect of the present invention, the radiation detector may further include dedicated wiring for reading the accumulated charges from the radiation detection pixels. Thus, radiation may be detected regardless of the radiation image imaging operations. Hence, radiation images may be imaged more quickly.

Thus, according to the tenth or eleventh aspect of the present invention, similarly to the invention in accordance with the first aspect, radiation irradiation states may be detected more accurately.

In the present invention, the characteristics of pixels for radiation detection are set in accordance with the imaging conditions. Therefore, even a case of imaging in a state in which an imaging target portion is offset from the central portion of an imaging region may be handled, and radiation irradiation states may be detected accurately even if, for example, an inflected portion such as an elbow or the like is to be imaged.

According to the present invention, pixels for radiation detection are configured with characteristics thereof being alterable, and the characteristics are set in accordance with imaging conditions of a radiation image. Thus, an effect is provided in that radiation irradiation conditions may be detected more accurately than in a case in which this setting is not performed.

What is claimed is:

1. A radiographic imaging device comprising:
   a radiation detector provided with
   a plurality of radiation image acquisition pixels that are arranged in an array in an imaging region of a radiation image, the radiation image acquisition pixels being configured to acquire information of pixels that form image information representing the radiation image by respectively converting irradiated radiation to charges and accumulating the charges, and
   a plurality of radiation detection pixels that detect a radiation state of irradiated radiation by respectively converting irradiated radiation to charges and accumulating the charges, the information acquired by the plurality of radiation detection pixels not forming image information representing the radiation image, the radiation detection pixels being disposed in the imaging region and a characteristic of the radiation detection pixels being alterable;
   an acquisition unit that acquires an imaging condition of the radiation image; and
   a setting unit that sets the characteristic in accordance with the imaging condition acquired by the acquisition unit;
   amplifiers that amplify signals represented by the charges accumulated by the radiation detection pixels by a pre-specified amplification ratio, wherein the setting unit sets the characteristic by setting the amplification ratio in accordance with the imaging condition; and
   a detection unit that detects the start of an irradiation of radiation and the end of an irradiation of radiation using mutually different radiation detection pixels,
   wherein the setting unit sets the amplification ratio of the amplifiers that correspond with the radiation detection pixels that are used for detecting the radiation irradiation start to be higher than the amplification ratio of the amplifiers that correspond with the radiation detection pixels that are used for detecting the radiation irradiation end.

2. The radiographic imaging device according to claim 1, further comprising low-pass filters that apply low-pass filtering with a pre-specified low-pass frequency to signals represented by the charges accumulated by the radiation detection pixels,
   wherein the setting unit sets the characteristic by setting the low-pass frequency in accordance with the imaging condition.

3. The radiographic imaging device according to claim 1, further comprising a switching unit that switches whether or not signals represented by the charges accumulated by the radiation detection pixels are combined in groups of a pre-specified number,
   wherein the setting unit sets the characteristic by switching whether or not the signals are combined in accordance with the imaging condition.

4. The radiographic imaging device according to claim 1, wherein the setting unit sets the characteristic in accordance with whether
   a radiation irradiation start or radiation irradiation end is to be detected
   or an irradiation amount of the radiation is to be detected on the basis of radiation detected by the radiation detection pixels.

5. The radiographic imaging device according to claim 1, wherein the imaging condition includes at least one of an imaging target portion, a region in which the imaging target portion is disposed during imaging of the radiation image, whether the imaging is of a video image or a still image, and an irradiation amount of radiation.

6. The radiographic imaging device according to claim 1, wherein the radiation detector further comprises dedicated wiring for reading the accumulated charges from the radiation detection pixels.

7. A radiographic imaging device comprising:
   a radiation detector provided with
   a plurality of radiation image acquisition pixels that are arranged in an array in an imaging region of a radiation image, the radiation image acquisition pixels being configured to acquire information of pixels that form image information representing the radiation image by respectively converting irradiated radiation to charges and accumulating the charges, and
   a plurality of radiation detection pixels that detect a radiation state of irradiated radiation by respectively converting irradiated radiation to charges and accumulating the charges, the information acquired by the plurality of radiation detection pixels not forming image information representing the radiation image, the radiation detection pixels being disposed in the imaging region and a characteristic of the radiation detection pixels being alterable;
   an acquisition unit that acquires an imaging condition of the radiation image; and
   a setting unit that sets the characteristic in accordance with the imaging condition acquired by the acquisition unit, wherein the setting unit sets the characteristic by switching between positions of the radiation detection pixels in accordance with the imaging condition;
   amplifiers that amplify signals represented by the charges accumulated by the radiation detection pixels by a pre-specified amplification ratio, wherein the setting unit sets the characteristic by setting the amplification ratio in accordance with the imaging condition; and
   a detection unit that detects the start of an irradiation of radiation and the end of an irradiation of radiation using mutually different the radiation detection pixels,
   wherein the setting unit sets the amplification ratio of the amplifiers that correspond with the radiation detection pixels that are used for detecting the radiation irradiation start to be higher than the amplification ratio of the amplifiers that correspond with the radiation detection pixels that are used for detecting the radiation irradiation end.

8. The radiographic imaging device according to claim 7, further comprising low-pass filters that apply low-pass filtering with a pre-specified low-pass frequency to signals represented by the charges accumulated by the radiation detection pixels,
   wherein the setting unit sets the characteristic by setting the low-pass frequency in accordance with the imaging condition.

9. The radiographic imaging device according to claim 7, further comprising a switching unit that switches whether or not signals represented by the charges accumulated by the radiation detection pixels are combined in groups of a pre-specified number,
  wherein the setting unit sets the characteristic by switching whether or not the signals are combined in accordance with the imaging condition.

10. The radiographic imaging device according to claim 7, wherein the setting unit sets the characteristic in accordance with whether
  a radiation irradiation start or radiation irradiation end is to be detected
  or an irradiation amount of the radiation is to be detected on the basis of radiation detected by the radiation detection pixels.

11. The radiographic imaging device according to claim 7, wherein the imaging condition includes at least one of an imaging target portion, a region in which the imaging target portion is disposed during imaging of the radiation image, whether the imaging is of a video image or a still image, and an irradiation amount of radiation.

12. The radiographic imaging device according to claim 7, wherein the radiation detector further comprises dedicated wiring for reading the accumulated charges from the radiation detection pixels.

13. A non-transitory computer-readable storage medium storing a program to be executed by a radiographic imaging device including a radiation detector that is provided with
  a plurality of radiation image acquisition pixels that are arranged in an array in an imaging region of a radiation image, the radiation image acquisition pixels being configured to acquire information of pixels that form image information representing the radiation image by respectively converting irradiated radiation to charges and accumulating the charges, and
  a plurality of radiation detection pixels that detect a radiation state of irradiated radiation by respectively converting irradiated radiation to charges and accumulating the charges, the information acquired by the plurality of radiation detection pixels not forming image information representing the radiation image, the radiation detection pixels being disposed in the imaging region and a characteristic of the radiation detection pixels being alterable;
  an acquisition unit that acquires an imaging condition of the radiation image; and
  a setting unit that sets the characteristic in accordance with the imaging condition acquired by the acquisition unit;
  amplifiers that amplify signals represented by the charges accumulated by the radiation detection pixels by a pre-specified amplification ratio, wherein the setting unit sets the characteristic by setting the amplification ratio in accordance with the imaging condition;
  a detection unit that detects the start of an irradiation of radiation and the end of an irradiation of radiation using mutually different radiation detection pixels,
  wherein the setting unit sets the amplification ratio of the amplifiers that correspond with the radiation detection pixels that are used for detecting the radiation irradiation start to be higher than the amplification ratio of the amplifiers that correspond with the radiation detection pixels that are used for detecting the radiation irradiation end; and
  wherein the program causes the radiographic imaging device to execute a process comprising:
  acquiring, by the acquisition unit, an imaging condition of the radiation image; and
  setting, by the setting unit, the characteristic in accordance with the acquired imaging condition.

14. A method for capturing a radiation image using a radiation detector that is provided with
  a plurality of radiation image acquisition pixels that are arranged in an array in an imaging region of a radiation image, the radiation image acquisition pixels being configured to acquire information of pixels that form image information representing the radiation image by respectively converting irradiated radiation to charges and accumulating the charges, and
  a plurality of radiation detection pixels that detect a radiation state of irradiated radiation by respectively converting irradiated radiation to charges and accumulating the charges, the information acquired by the plurality of radiation detection pixels not forming image information representing the radiation image, the radiation detection pixels being disposed in the imaging region and a characteristic of the radiation detection pixels being alterable;
  an acquisition unit that acquires an imaging condition of the radiation image; and
  a setting unit that sets the characteristic in accordance with the imaging condition acquired by the acquisition unit;
  amplifiers that amplify signals represented by the charges accumulated by the radiation detection pixels by a pre-specified amplification ratio, wherein the setting unit sets the characteristic by setting the amplification ratio in accordance with the imaging condition;
  a detection unit that detects the start of an irradiation of radiation and the end of an irradiation of radiation using mutually different radiation detection pixels,
  wherein the setting unit sets the amplification ratio of the amplifiers that correspond with the radiation detection pixels that are used for detecting the radiation irradiation start to be higher than the amplification ratio of the amplifiers that correspond with the radiation detection pixels that are used for detecting the radiation irradiation end;
  the method comprising:
  acquiring, by the acquisition unit, an imaging condition of the radiation image; and
  setting, by the setting unit, the characteristic in accordance with the acquired imaging condition.

* * * * *